(12) United States Patent
Seigfried

(10) Patent No.: US 9,005,626 B2
(45) Date of Patent: Apr. 14, 2015

(54) LIQUID COMPOSITIONS CAPABLE OF FOAMING AND INCLUDING ACTIVE AGENTS, AND METHODS FOR MAKING OR DEVELOPING SAME

(75) Inventor: Bernd G. Seigfried, Limburgerhof (DE)

(73) Assignee: MIKA Pharma GmbH, Speyer (DE)

( * ) Notice: Subject to any disclaimer, the term of this patent is extended or adjusted under 35 U.S.C. 154(b) by 223 days.

(21) Appl. No.: 12/838,737

(22) Filed: Jul. 19, 2010

(65) Prior Publication Data

US 2011/0059117 A1 Mar. 10, 2011

(30) Foreign Application Priority Data

Jul. 24, 2009 (DE) .......................... 10 2009 034 603

(51) Int. Cl.
*A61K 31/7048* (2006.01)
*A61K 9/12* (2006.01)
*A61K 9/00* (2006.01)

(52) U.S. Cl.
CPC ............... *A61K 9/122* (2013.01); *A61K 9/0014* (2013.01)

(58) Field of Classification Search
CPC .................................. A61K 9/14; A61K 9/122
USPC ................................ 424/184.1, 278; 514/159
See application file for complete search history.

(56) References Cited

U.S. PATENT DOCUMENTS

| | | | |
|---|---|---|---|
| 4,983,765 A | 1/1991 | Lukas et al. | |
| 5,004,611 A | 4/1991 | Leigh | |
| 5,200,198 A | 4/1993 | Geisslinger et al. | |
| 5,206,029 A | 4/1993 | Geisslinger et al. | |
| 5,369,131 A | 11/1994 | Poli et al. | |
| 5,556,638 A | 9/1996 | Wunderlich et al. | |
| 5,560,924 A | 10/1996 | Wunderlich et al. | |
| 5,565,613 A | 10/1996 | Geisslinger et al. | |
| 5,738,869 A | 4/1998 | Fischer et al. | |
| 5,747,058 A | 5/1998 | Tipton et al. | |
| 5,958,379 A | 9/1999 | Regenold et al. | |
| 5,976,566 A | 11/1999 | Samour et al. | |
| 6,066,332 A | 5/2000 | Wunderlich et al. | |
| 6,165,500 A | 12/2000 | Cevc | |
| 6,287,592 B1 | 9/2001 | Dickinson | |
| 6,309,663 B1 | 10/2001 | Patel et al. | |
| 6,464,987 B1 | 10/2002 | Fanara et al. | |
| 6,605,298 B1 | 8/2003 | Leigh et al. | |
| 6,645,520 B2 | 11/2003 | Hsu et al. | |
| 6,835,392 B2 | 12/2004 | Hsu et al. | |
| 7,244,447 B2 | 7/2007 | Hsu et al. | |
| 7,473,432 B2 | 1/2009 | Cevc et al. | |
| 2002/0039756 A1 | 4/2002 | Bang et al. | |
| 2003/0078172 A1 | 4/2003 | Guiramand et al. | |
| 2003/0170194 A1 | 9/2003 | Piotrowiak et al. | |
| 2004/0037876 A1 | 2/2004 | Geisslinger et al. | |
| 2005/0043280 A1 | 2/2005 | Geisslinger et al. | |
| 2005/0079139 A1* | 4/2005 | Jacques et al. | .................. 424/47 |
| 2005/0220857 A1 | 10/2005 | Purpura et al. | |
| 2007/0224153 A1* | 9/2007 | LiBrizzi et al. | ................. 424/74 |
| 2007/0231353 A1* | 10/2007 | Gilbard et al. | ................ 424/400 |
| 2008/0233183 A1 | 9/2008 | McCook et al. | |
| 2009/0162421 A1 | 6/2009 | Geisslinger et al. | |
| 2011/0269704 A1 | 11/2011 | Seigfried | |
| 2011/0269851 A1 | 11/2011 | Bortlik et al. | |
| 2013/0309215 A1 | 11/2013 | Seigfried | |

FOREIGN PATENT DOCUMENTS

| | | | | |
|---|---|---|---|---|
| DE | 19520659 A1 | 12/1996 | | |
| DE | 19740095 C2 | 3/1999 | | |
| DE | 19949922 C1 | 5/2001 | | |
| DE | 102010027315 A1 | 1/2011 | | |
| EP | 0510561 A1 | 10/1992 | | |
| EP | 0521398 A2 | 1/1993 | | |
| EP | 0704206 A1 | 4/1996 | | |
| EP | 1092970 A2 | 4/2001 | | |
| IT | EP 0510561 A1 * | 10/1992 | ............... | A61K 9/12 |
| WO | WO-93/10760 A1 | 6/1993 | | |
| WO | WO-93/10771 A1 | 6/1993 | | |
| WO | WO-98/02184 A1 | 1/1998 | | |
| WO | WO-98/475802 A1 | 10/1998 | | |
| WO | WO-00/50019 A2 | 8/2000 | | |
| WO | WO-00/74670 A1 | 12/2000 | | |
| WO | WO-2009/083115 A1 | 7/2009 | | |
| WO | WO-2011/009436 A2 | 1/2011 | | |

OTHER PUBLICATIONS

Definition of phospholipid—download from http://www.biology-online.org/dictionary/Phospholipid, Feb. 25, 2014*

(Continued)

*Primary Examiner* — Johann R Richter
*Assistant Examiner* — Yanzhi Zhang
(74) *Attorney, Agent, or Firm* — Goodwin Procter LLP

(57) ABSTRACT

A liquid composition suitable for topical use comprising is provided that includes a phospholipid foaming agent and at least one solvent; and a pharmaceutically acceptable active agent; wherein the liquid composition is capable of mechanically foaming without an additional propellant; and wherein upon mechanical foaming of 250 ml of the liquid composition results in a foam with a foam volume of at least about 400 ml and a foam stability wherein at least about 50% of the foam volume is still present after about 5 minutes at 25° C., as determined using a SITA foam measurement. Also provided herein are methods of making disclosed compositions and methods of use.

20 Claims, 19 Drawing Sheets

(56) References Cited

OTHER PUBLICATIONS

Author: Sonja Hoeller Hoeller; et al, Title: Multinuclear NMR characterisation and dermal delivery of fluorinated drugs in soybean-microemulsion systems; Journal or Book Title: Journal of pharmaceutical sciences Volume and Issue No. 98, pp. 2686-2695; Publication Date: 2009.*

Brunner, M., et al., "Favourable Dermal Penetration of Disclofenace after Administration to the Skin Using a Novel Spray Gel Formulation," British Journal of Clinial Pharmacology (2005) pp. 1-5.

Eisvogel, M., "Whipping up Cosmetic Foams", Cossma: Cosmetics, Spray Technology, Marketing, Braun Fachverlage, Karlsruhe, DE, (2001, pp. 56, 58.

International Search Report for PCT/DE2010/000818 mailed on Jul. 7, 2011.

Tarenflurbil, from Wikipedia, printed Mar. 26, 2010.

Wendel, A., "Lecithin," (1995) Kirk-Othmer Encyclopedia of Chemical Technology, Fourth Edition, vol. 15, pp. 192-210.

Predel et al., "A randomized, double-blind, placebo-controlled multicentre study to evaluate the efficacy and safety of diclofenac 4% spray gel in the treatment of acute uncomplicated ankle sprain", J. Int'l. Med. Res., 41(4):1187-1202 (2013).

Public Assessment Report—Diclofenac Sodium 4% Spray Gel, Mika Pharma GmbH (Mar. 20, 2006).

Written Opinion for PCT/DE2010/000818 dated Jan. 24, 2012 (English Translation).

Guo et al., "Enzymatic modificatiton of phospholipids for functional applications and human nutrition", Biotech Advances, 23:203-259 (2005).

* cited by examiner

LIQUID COMPOSITIONS CAPABLE OF FOAMING AND INCLUDING ACTIVE AGENTS, AND METHODS FOR MAKING OR DEVELOPING SAME

RELATED APPLICATION

This application claims priority to German patent application DE10-2009-034-603.1, filed Jul. 24, 2009, and hereby incorporated by reference in its entirety.

FIELD

The present disclosure is directed in part to a method for making or developing liquid pharmaceutical compositions to be applied as a foam to the skin, and topically applicable compositions.

BACKGROUND

Topically applied pharmaceutical compositions that exist in the liquid state and are present as a foam when applied are familiar. For example, EP 0 510 561 B1 describes one such pharmaceutical composition applied as foam, wherein the basic liquid used in the known pharmaceutical composition is foamed exclusively by mechanical action. The basic liquid composition that is mechanically foamed contains, as ingredients, a surfactant as the foaming agent, a solvent or mixture of solvents, as well as a pharmaceutical active ingredient, wherein this known liquid composition should be foamable simply by mechanical action, without the use of a propellant. In example 5 of EP 0 510 561 B1, one such known composition is described, containing an aqueous alkylamidobetaine solution as the surfactant. In addition, the composition described in this example is provided with lecithin, which serves solely to form liposomes.

In order to be able to measure the foaming behavior of liquid compositions, various measurement techniques are known and also standardized, such as by DIN Standard 53902. The particular liquid composition being investigated is subjected to a more or less reproducible mechanical action for a given time in order to create a foam, whose volume and stability are measured. According to DE 197 40 095 A, however, known measurement techniques do not adequately distinguish between the foam volumes and foam stabilities of compositions which are similar in terms of their ingredients. DE 197 40 095 A proposes foaming the liquid composition being measured by using a stirrer with a given profile, which is driven at a given speed of rotation. The foam created in this way is visually measured.

A further development of this foam measuring technique is described in EP 1 092 970 B1, wherein the development differs from the measurement technique previously described in reference to DE 197 40 095 A by providing an automatic determination of the height of the foam via measuring electrodes. This measurement method, which is called the "SITA measurement method" in the present text, allows one to determine the foam volume on the one hand, and on the other hand the foam stability of liquids, especially dyeing and cleaning solutions, electroplating agents, emulsions, rinsing agents, body care products or even beer, so as to obtain a quality rating of the aforementioned foamable liquids.

When one needs to develop liquids that are foamable and therefore are applied as a foam in the field of pharmacy, it is usually proposed to proceed by selecting a pharmaceutically active liquid and one then attempts to foam it by varying the mechanical foaming technique, in particular, by varying the air pressure, the geometry and configuration of the foam head and the valve of a particular foam applicator. However, such a development process for foamable, originally liquid, pharmaceutical compositions is very time intensive and may suffer from a drawback such that a foam differing in composition and essentially inhomogeneous can result from varying the configuration of the aforementioned parameters of the mechanical foam applicator.

Thus, one underlying problem of the present invention is to provide a method for the development of a liquid pharmaceutical composition to be applied as foam to the skin, by which the development time for such pharmaceutical compositions is substantially simplified and shortened. Further, another underlying problem of the present invention is to provide a topically applicable composition that can be applied as foam and that contains a systemically or topically acting pharmaceutical active ingredient, and, may be, for example, be developed by the disclosed processes.

SUMMARY

Provided herein is a liquid composition suitable for topical use comprising: a phospholipid foaming agent and at least one solvent; a pharmaceutically acceptable active agent; wherein the liquid composition is capable of mechanically foaming without an additional propellant; and wherein upon mechanical foaming of 250 ml of the liquid composition results in a foam with a foam volume of at least about 400 ml (e.g., about 450 to about 1400 mL or about 600 mL to about 1200 mL) and a foam stability wherein at least about 50% of the foam volume is still present after about 5 minutes at 25° C., (e.g., about 55% to about 85% of the foam volume is present after 5 minutes, or about 85% toa bout 100% of the foam volume is still present after about 10 minute) as determined e.g., using a SITA foam measurement.

Also provided herein, in one embodiment, is a method for making a foamable liquid composition for topical use, comprising: a. providing a liquid composition comprising at least one pharmaceutically active agent, at least one solvent, and a foaming agent; b. mechanically creating a foam of the liquid composition; c. scanning the foam surface to determine the stability and the volume of the foam; d. varying the concentration of at least one of the pharmaceutically active agent, the solvent, or the foaming agent; and e. repeating steps b and c, if needed, until 250 ml of the liquid composition, after the mechanical creation of the foam, has a foam volume of at least 400 mL and a foam stability wherein at least about 50% of the foam volume is still present after about 5 minutes at 25° C.

In a provided method of development of a liquid pharmaceutical composition to be applied as a foam to the skin, having as minimum components a solvent, a pharmaceutical active ingredient, and a foaming agent, the method includes foam volume and the foam stability to be determined by a standardized SITA measurement method, wherein no propellant is used in this measurement method. For example, in a provided liquid pharmaceutical composition, the at least one foaming agent, the at least one solvent and the at least one pharmaceutical active ingredient are varied in regard to their chemical nature and/or concentration until the foam created by the SITA measurement method under standardized conditions has a foam volume of at least 400 ml, especially a foam volume between 450 and 1400 ml, and preferably a foam volume between 600 and 1200 ml. Furthermore, the foam according to a method of the invention must have such a foam stability that it still has, after a dwell time of up to ten minutes and especially after a dwell time of up to five minutes, at least 50% of the foam volume and especially between 55% and 100% of the foam volume and preferably between 85% and 99% of the foam volume that was originally present immediately after the creation of the foam. In other words, therefore, the development method according to the invention calls for varying the minimum ingredients (solvent, pharmaceutical active ingredient, and foaming agent) contained in the liquid pharmaceutical composition that is supposed to form the foam when applied in terms of their chemical nature and/or their concentration until they give rise to a foam by the SITA measurement method under standardized conditions whose foam volume possesses the previously quantified volumes and whose foam stability possesses the previously quantified stabilities.

The above-described method of the invention has a number of advantages. Thus, it has been established, surprisingly, that the method of the invention enables an especially easy and rapid development of such liquid pharmaceutical compositions as can be reproducibly foamed with a number of foam applicators, so that unlike the prior art described at the outset one can develop pharmaceutical foams that are especially reproducible in terms of their foam consistency and their foam composition. For example, if the goal of such a development is to provide a liquid composition whose foam should have a relatively short stability after being foamed by means of a suitable mechanical foam applicator, so that it quickly breaks down after being applied to the skin, in the method of the invention one will vary the chemical nature and/or the concentration of the ingredients until a foam results in the SITA measurement method whose foam stability is distinguished in that, within two to four minutes, the foam volume still takes on a value between 50% and 70% of the original foam volume. In contrast, when the objective is to create an especially stable foam, the chemical nature and/or the concentration of the minimum ingredients of the liquid composition which afterwards forms the foam will be varied so that a foam results whose foam stability is so high that after eight to ten minutes there is still present between 85% and 99% of the foam volume that was originally present immediately after the foaming process. If, on the other hand, a liquid, foamable composition which has an especially large foam volume is desired, then the nature and/or the concentration of the minimum ingredients of the liquid composition will be varied so that an especially high foam volume results in the SITA measurement method, i.e., a foam volume that varies between 600 ml and 1200 ml or even up to 1400 ml.

For example, a method of the invention proposes a standardized method in which, by variation of the chemical nature of the ingredients and/or their concentration, one can develop a foam quantified in the above sense with regard to the foam volume and the foam stability, and which can accordingly be applied to the skin of humans and animals.

It should be noted for clarification that the term skin in the sense of the present specification covers not only the actual skin, but also the mucous membrane in mouth, nose, vagina or foreskin, the areas of the ear and especially the areas of the inner ear, the area of the anus and the rectum, the area of the eyes, especially the area under the eyelid, such as the conjunctiva, cornea and lacrimal sac, the nails and scalp, these being the preferred sites of application of the foam developed according to the invented method. The term "and/or" used in the present specification means that all or some elements of the particular listing are to be construed additively or that some or all elements of the respective listing are to be construed alternatively. Moreover, it should be stated that all terms used in the singular case in the present specification of invention also include the plural of these terms.

DETAILED DESCRIPTION

Figure 1:
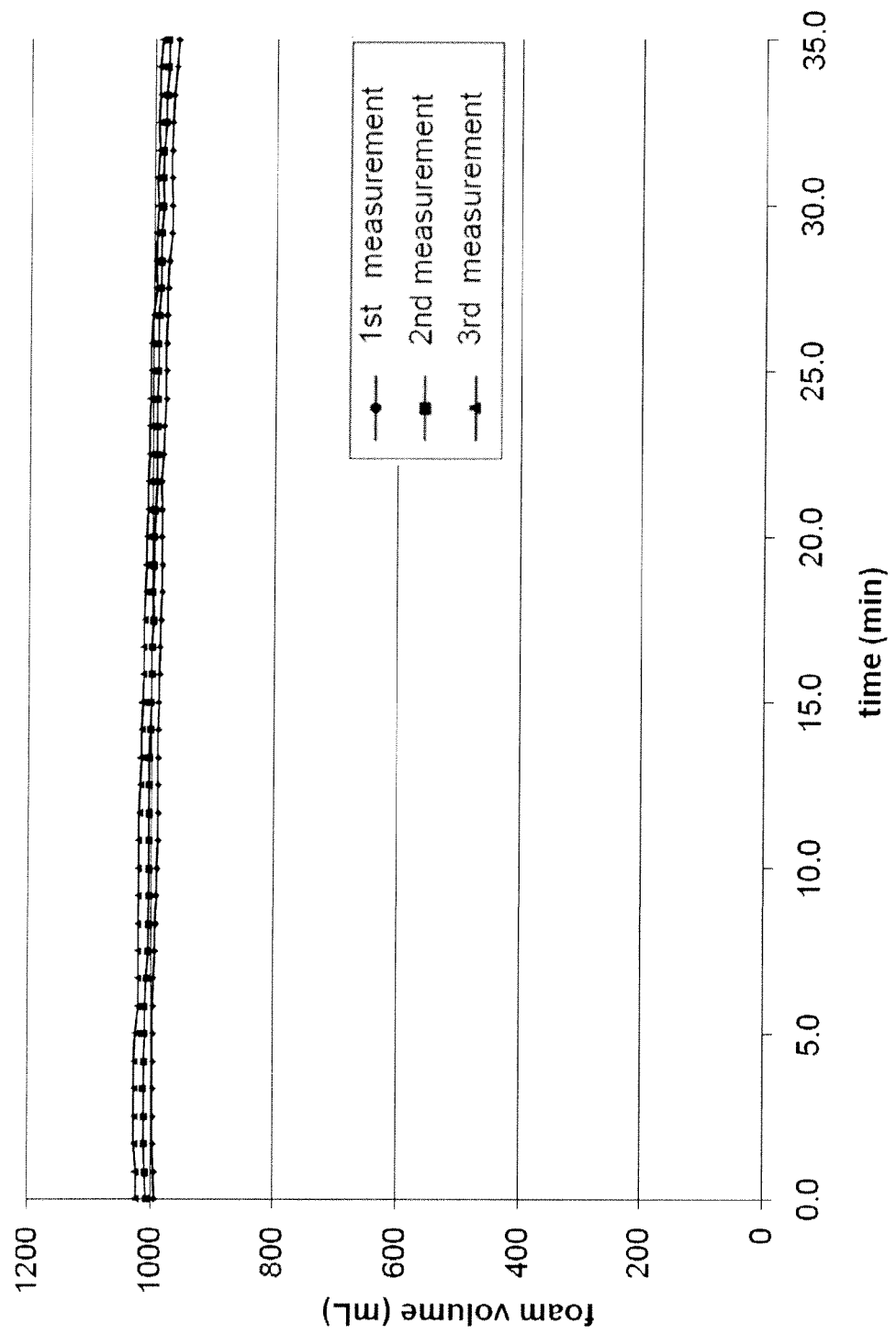
FIGS. 1-16 depicts 3 measurements (as indicated in the legend) foam volume in mL (y-axis) vs. time (minutes) for various compositions as described herein.

In an embodiment, disclosed methods relate to method of development of a liquid pharmaceutical composition to be applied as a foam to the skin calls that include producing a correlation between the foam as specified by the SITA measurement method and the desired pharmaceutical properties. By desired pharmaceutical properties is meant in particular the transport of active ingredient through the layers of the foam into and/or through the skin, i.e., the permeation and/or penetration of the skin and/or the fine distribution of the active ingredient and/or the resulting pharmaceutical effect. For example, if a goal of the development in the method of the invention is, for example, that the active ingredient should quickly get onto the skin surface in relatively high concentration, one will vary the nature and/or concentration of the ingredients in the liquid composition being foamed by the SITA measurement method so that the resulting foam has a relatively small foam volume, especially a foam volume between 450 ml and 600 ml, and a relatively low foam stability, especially a foam stability after five minutes between 55% and 70% of the foam volume that was originally present immediately after creating the foam.

In a modification of the above specified embodiment of the invented method, another embodiment calls for selecting a foam applicator for the mechanical foaming of the liquid composition, a foam is created from the liquid composition by the selected foam applicator, and a correlation is produced between the properties, especially the pharmaceutical properties of the foam created via the foam applicator and the foam volume and/or the foam stability as determined via the SITA measurement method. This embodiment of the invented method allows one to develop foams with defined foam volumes and foam stabilities, as measured by the SITA measurement method, especially easily and quickly by varying the nature and/or the concentration of the ingredients of the liquid pharmaceutical composition, which then correlate with the foams that are later applied as foam to the skin by the selected foam applicator.

Especially when the development method of the invention is used to create a foam from the liquid composition that possesses a foam density between 0.05 g/ml and 0.8 g/ml, preferably between 0.15 g/ml and 0.4 g/ml by the SITA measurement method, it has been found that such liquid compositions provide excellent foams that can be applied with a number of differently designed, mechanical-type foam applicators.

In an embodiment, the chemical nature and/or the concentration of ingredients (solvent, foaming agent, active ingredient) are varied in the method of the invention so as to ensure the foam volume and the foam stability as indicated above in the development method of the invention. In particular, the solvent for the production of the liquid composition in the method of the invention may be chosen from the group consisting of: water, at least one alcohol, especially at least one monovalent to trivalent alcohol, at least one polyalcohol and mixtures of the aforementioned solvents. Of course, in choosing the solvent one will make sure that these solvents are skin-tolerated and especially do not result in any skin irritation, so that they are appropriately pharmaceutically applicable. Preferred solvents are 2-propanol, propylene glycol, glycerin as well as polyols, while the term water comprises all aqueous systems, especially also aqueous pharmaceutical buffer systems.

In an especially suitable embodiment of the method of the invention, the pharmaceutical active ingredient is used as the foaming agent, so that this embodiment of the invented method is based on the fact that it contains, besides the solvent, only the pharmaceutical active ingredient whose concentration and whose chemical nature are varied so that the foam volumes and foam stabilities indicated in the method of the invention and measured according to the SITA method are guaranteed.

Alternatively or in addition to this, a modification of the method of the invention proposes that the foaming agent for the production of the liquid composition is chosen from the group comprising surfactants, especially anionic, cationic, nonionic and ampholytic surfactants, silicones, fats, fatty acids, fatty acid derivates, phospholipids, sugar derivates, lipids, especially sphingolipids and glycolipids, and mixtures and derivates of the aforementioned substances.

Foaming agents, whether the active ingredient itself or the above listed foaming agents, may be capable of provide the aforementioned foam volumes and foam stabilities as soon as the liquid composition is foamed in purely mechanical fashion, without the use of a propellant. Preferred surfactants include the fatty alkyl ether sulfates, the alkyl phosphates, the alkyl ether phosphates, the alkyl benzene sulfonates, the petroleum sulfonates, the olefin sulfonates and/or the esters of sulfosuccinic acid. Among the silicones, one should mention especially modified siloxanes, polydialkyl siloxanes and preferably linear or cyclical polydimethyl siloxanes. Fats and modified fats, such as fatty acids, fatty acid derivatives, fatty acid esters, as well as synthetic, plant and animal phospholipids, especially phosphatidyl choline and/or hydrogenated phospholipids and preferably hydrogenated phosphatidyl choline, are among the preferred foaming agents, in addition to the sphingolipids, glycolipids and sugar derivates, preferably sugar or sorbitol esters.

Among the fat derivatives, especially the sulfates of fatty acids, sulfonates of fatty acids, salts of sulfates of fatty acids, salts of sulfonates of fatty acids, soaps and mixtures and derivates of the aforementioned substances are especially suitable as foaming agents for use in the method of the invention. This holds likewise for alkoxylated fatty acids and alkoxylated fatty acid derivatives, alkoxylated fatty alcohols, alkoxylated phenols as well as mixtures and derivates of the aforementioned substances.

Furthermore, preferred surfactant foaming agents are chosen from the group consisting of: alkylcarboxylates, alkylsulfates, alkylsulfonates, alkylethercarboxylates, sulfates of fatty acids, phosphates of fatty acids, sulfonates of fatty acids, salts of sulfates of fatty acids, salts of sulfonates of fatty acids, fatty acid amides, polyalkylenes, fluorosurfactants, soaps, metal soaps, especially alkaline soaps, such as sodium, potassium and ammonium salts of aliphatic carboxylic acids, organic amino-soaps, especially organic amine soaps of aliphatic carboxylic acids, quaternary ammonium compounds, especially benzalkonium chloride, octadecylammonium chloride, sulfonium salts, amidoamines, fatty acid esters, preferably monoglycerin, diglycerin and triglycerin esters, fatty acid ethers, alkoxylated, especially ethoxylated fatty acids, alkoxylated, especially ethoxylated fatty acid derivates, alkoxylated, especially ethoxylated fatty alcohols, alkoxylated, especially ethoxylated phenols, alkoxylated, especially ethoxylated fatty acid amides, mono- and dialkylalkanolamides or alkylpolyglucosides, especially coco-mono-ethanolamides, coco-di-ethanolamides, coco-mono-isopropanolamides, coco-diglucosides, betaine, betaine derivates, preferably N-alkylbetaine, alkyl-amidopropylbetaine, sulfobetaine, alkylsulfobetaine, alkylglycinate and alkylcarboxyglycinates, wherein the alkyl residue each time comprises in particular a carbon skeleton with 8 to 18 carbon atoms, acylamino acid, alkylimidazoline, N-substituted alkylamines, acyllactate, N-acylsarkosinate, alkanolamide, aminoxide, polyhydroxyalcohol esters, as well as mixtures and derivates of the aforementioned substances.

As cationic surfactants that are likewise especially suitable as the foaming agent in the method of the invention for the production of the liquid composition, one will select substances which contain quaternary ammonium bonds, sulfonium salts, amidoamides and their mixtures as well as their derivates.

Preferred ampholytic surfactants for the production of the liquid composition will be chosen from the group comprising betaine and betaine derivates.

As for the active ingredients used in the method of the invention, these will preferably be active ingredients such as are described in further detail in connection with the topically applicable composition according to the invention.

Besides the repeatedly aforementioned solvent, the pharmaceutical active ingredient and the foaming agent, in further embodiments of the invented method for production of the liquid composition that is foamed in purely mechanical fashion for its application, there is proposed in particular a complexing agent, a buffer, a thickening agent, an antioxidant and/or a stabilizer. However, one must make pay heed that these aforementioned ingredients can also have an influence on the foam volume and the foam stability, but this can be determined quite easily and without problem and within the shortest time in a reproducible manner by the method of the invention.

As already mentioned above, the present invention furthermore concerns a topically applicable composition.

The topically applicable composition of the invention, which is developed preferably but not exclusively according to the above described method of the invention, has, a pharmaceutical active ingredient, a solvent as well as a foaming agent. In contrast to the known liquid composition of EP 0 510 561 for example, which is applicable as a foam, the topically applicable composition of the invention proposes a phospholipid foaming agent as the foaming agent. Furthermore, the at least one phospholipid foaming agent, the at least one solvent and the at least one active ingredient in the composition of the invention are attuned to each other in their chemical nature and/or their concentration so that the composition can be mechanically foamed exclusively without the use of an additional propellant. The foam so created by the mechanical foaming during the application has a foam volume of at least 400 ml, preferably between 450 and 1400 ml and especially a foam volume between 600 and 1200 ml. Furthermore, the composition according to the invention has such a foam stability that the foam still has, after a dwell time of up to ten minutes and especially after a dwell time of up to five minutes, at least 50% of the foam volume and especially between 55% and 100% of the foam volume and preferably between 85% and 99% of the foam volume that was originally present immediately after the creation of the foam, wherein both the aforementioned foam volume and the aforementioned foam stability can be determined by the standardized SITA foam measurement method. In other words, topically applicable composition of the invention is characterized not only by the nature of its ingredients and/or their concentration, but also by the foam created from it, wherein the foam is specified and quantified in terms of the foam volume and the foam stability by the standardized SITA measurement method.

The composition of the invention has a number of advantages. When the composition of the invention is applied to human or animal skin, where the term skin as already defined above covers the mucous membranes of mouth, nose, vagina and foreskin, the skin areas of the ear and especially the inner ear, the skin areas of the anus and the rectum, the nails and the eyes, especially the conjunctiva, the cornea and the lacrimal sac, the foam created from the composition of the invention has, first of all, an excellent adhesion to these application sites, so that it cannot easily be wiped off unintentionally. Moreover, the foam produced in exclusive mechanical fashion from the liquid composition of the invention has a naturally homogeneous composition, and the pharmaceutical active ingredient is present in this foam in an especially uniform ultrafine distribution, so that once the foam breaks down after being applied this ultrafine distribution is retained in the liquid layer formed on the skin surface, with the result that the pharmaceutical active ingredient is transported with a high rate of penetration and/or permeation into and/or through the skin. This, in turn, means that the active ingredient so applied has a high pharmaceutical efficacy, so that if desired the concentration of active ingredient in the composition of the invention can be reduced as compared to traditional compositions or, alternatively, the time intervals between consecutive applications can be lengthened appropriately, especially since the active ingredient forms a depot in the skin. Due to the fact that a phospholipid foaming agent is present as the foaming agent in the composition of the invention, this phospholipid foaming agent has the effect of producing a faster penetration or permeation into or through the skin, which proves to be an additional advantage of the composition of the invention.

Especially when the foam created from the composition of the invention by the SITA measurement method has a foam density between 0.05 g/ml and 0.8 g/ml, preferably between 0.15 g/ml and 0.4 g/ml, such embodiments of the compositions according to the invention have the aforementioned advantageous properties to an enhanced degree.

As already explained above for the method of the invention, the composition according to the invention may include, as a solvent, especially water, at least one alcohol, especially at least one polyvalent to trivalent alcohol, and/or at least one polyalcohol, and such solvents are chosen in particular for such phospholipid foaming agents as contain a phospholipid and/or a phospholipid mixture isolated from plant components, especially soy beans.

For clarity it is pointed out that the term phospholipid mixture or phospholipids in the above description covers all phospholipids of plant origin, animal origin, or synthetic origin. In particular, this includes the ester phospholipids, especially phosphatidyl choline, lyso-phosphatidyl choline, phosphatidyl ethanolamine, lyso-phosphatidyl ethanolamine, phosphatidyl serine, lyso-phosphatidyl serine, phosphatidyl inositol, lyso-phosphatidyl inositol, phosphatidyl glycerin, diphosphatidyl glycerin and the phosphatidic acids, the ether phospholipids, especially choline plasmalogen and ethanol aminoplasmalogen, as well as the sphingosine phospholipids, especially ceramide phosphoryl choline and phytoglycolipid and derivates of the ester phospholipids, the ether phospholipids and/or the sphingosine phospholipids, regardless of whether they have been isolated from natural substances, such as plants or plant components, especially plant seeds, or animal components, such as eggs, or synthetically produced. Typical derivates of these phospholipids which can be contained in the composition of the invention as foaming agent are preferably the hydrogenated or partly hydrogenated phospholipids, especially hydrogenated or partly hydrogenated phosphatidyl choline.

Regarding the active ingredient, it should be noted that the at least one active ingredient contained in the composition of the invention is one that is suitable for use on humans or animals and especially for topical and systemic application, especially on the skin, wherein an especially preferred active ingredient is chosen from the group comprising local anesthetics, anti-allergic agents, dermatics, active ingredients against flu infections and colds, active ingredients for the treatment of neuropathies, active ingredients for the treatment of disturbed circulation, chemotherapy drugs, quinine, antimycotics, antibiotics, thalidomide, serotonin, eicosanoids, analgesics, anticonvulsants, nonsteroidal antirrheumatics, leukotrienes, leukotriene inhibitors, androgens, antiandrogens, corticoids, opiate receptor antagonists, blood clotting inhibitory substances, thrombocyte aggregation inhibitors, histamine antagonists, regulatory and enzymatically acting peptides and proteins, nucleic acids (single and double-stranded DNA, single and double-stranded RNA, snRNA, DNA oligonucleotides, RNA oligonucleotides) and oligopeptides, antipruritics, antidiabetics, prostaglandins, prostaglandin synthesis inhibitors, antiviral-acting or virostatic-acting substances, antimicrobial-acting substances, active ingredients against prions, immune suppressants, hormones, active ingredients for treatment of warts or wounds, especially chronic wounds, vitamins, plant extracts or essences of plant extracts, psychoactive drugs, active ingredients influencing sleep, analeptics, general anesthetics, muscle relaxants, antiepileptics, antiparkinson agents, antiemetics, antiparasitics, ganglion-active substances, sympathetic-active substances, parasympathetic-active substances, antibacterial-acting drugs, calcium antagonists, cardiovascular agents, antiasthmatics, antitussives, expectorants, hepatics, diuretics, choleretics, disinfectants, trace elements, antiinfectives, cytostatics, antimetabolites, hormone antagonists, immune modulators, as well as derivates and salts of the aforementioned active ingredients.

Depending on the particular use of the invented composition, disclosed compositions can include an active substance or a special active substance mixture, which is chosen from the following listed special active substances, presented under their particular main groups Preferably, for the main group of the 5α-reductase inhibitors, alphatradiol and 17α-estradiol can be used; for the main group of weight loss agents, appetite curbing or antiobesity agents: norephedrine, phenylpropanole amine, D-norpseudoephedrin, orlistate and sibutramine; for the main group of ACE-inhibitors: benazepril, cilazapril, quinapril, ramipril, spirapril and trandolapril; for the main group of acidosis therapeutic or antihypoxemic agents: calcium-satrium-hydrogen-citrate; for the main group of astringents: aluminium chloride, aluminum diacetate, aluminum formate, bismuth chloride oxide, bismuth gallate, polycresulene, tannin and zinc oxide; for the main group of acne agents: azelainic acid and benzoyl peroxide; for the main group of aldosterone antagonists: canrenionic acid, potassium canrenoate, dolasetrone and eplerenone; for the main group of alcohol withdrawal agents: acamprosate and disulfiram; for the main group of α1-receptor blockers: alfuzosin, bunazosin and dihydroergotamine; for the main group of α2-receptor agonist: apraclonidine, brimonidine, doxozosine and moxonidine; for the main group of α- and β-sympathomimetics: adrenaline, dobutamine, dopexamine and epinephrine; for the main group of aminoglycoside antibiotics: gentamycin, kanamycin, neomycin, netilmycin, streptomycin and tobramycin; for the main group of amino acids: alanine, aminoacetic acid, glycine, arginine, asparagine, asparaginic acid, cysteine, cystine, glycocoll, ornithine, proline and serine; for the main group of amino acid substitution: alanylglutamine, arginine glutamate, desmeninol, glycyl glutamine and glycyl tyrosine; for the main group of analeptics or antihypoxemics: camphor and caffeine; for the main group of analgesics or antirheumatics: abatacept, acetylsalicylic acid, acetaminophen, ademetionin, anakinra, aurothiomalate sodium, buprenorphin, diethylamine salicylate, etanercept, etoricoxide, fentanyl, flufenamine acid, flupirtin, glucosamine, hydromorphone, 2-hydroxybenzoic acid, diethylazane salt, hydroxychloroquin, hydroxyethylsalicylate, leflunomide, levomethadone, meptazinol, metamizol, methylsalicylate, misoprostol, morphine, nalbuphin, sodium aurothiomalate, nicoboxil, nonivamide, noramidopyrine, novaminsulfone, oxaceprol, oxycodone, paracetamol, penicillamine, pethidine, phenazone, piritramide, propylnicotinate, propyphenazone, salazosulfapyridine, sulfasalazine, tilidine, tramadol and ziconotide; for the main group of acidification agents: malic acid; for the main group of antacids: almasilate, aluminum hydroxide, aluminum hydroxide-magnesium carbonate gel, aluminum phosphate, carbaldrate, magaldrate, magnesium carbonate, magnesium hydroxide and magnesium trisilicate; for the main group of antihelminthics: albendazol, mebendazol, niclosamide, praziquantel, pyrantel and pyrviniumembonate; for the main group of antiallergics: chromoglycinic acid, lodoxamide, mequitazine, mizolastine and olopatadine; for the main group of antianemics: calcium folinate, darbepoeton alpha, iron, iron carboxymaltose, iron (II) chloride, iron (II) fumarate, iron (II) gluconate, iron (II) succinate, iron (II) sulfate, iron glycine sulfate, iron (III) hydroxide-dextran complex, iron (III) hydroxide-polymaltose complex, iron (III) hydroxide-saccharose complex, iron (III) sodium-gluconae complex, epoetin alpha, epoetin beta, epoetin zeta, erythropoetin, folic acid and methoxy-polyethylglycol-epoetin beta; for the main group of antiandrogens: bicalutamide, chlormadione and cyproterone; for the main group of antiarrhythmics: ajmalin, amiodaron, quinidine, detajmium bitartrate, flecainide, lidocaine, mexiletin, orciprenalin, prajamalium bitartrate, propafenon and sotalol; for the main group of antibiotics or anti-infectives: amikacin, aminosidine, paromomycin, chloramphenicol, ciprofloxacin, clindamycin, colistimethate-sodium, colistin, enfuvirtid, enoxacin, flucloxacillin, fosfomycin, fusafungin, levofloxacin, linezolid, mefloquin, metronidazol, mezlocillin, moxifloxacin, norfloxacin, ofloxacin, oxacillin, penicillin G, penicillin V, phenoxymethylpenicillin, phenoxymethylpenicillin-benzathin, pipemidinic acid, piperacillin, piperacillin+tazobactam, proguanil, propicillin, pyrimethamine, retapamulin, rifaximin, roxithromycin, sulbactam, sulbactam+ampicillin, sulfadiazine, spiramycin, sultamicillin, tazobactam+piperacillin, teicoplanin, telithromycin, tigecyclin and vancomycin; for the main group of antidementia agents (nootropics): galantamine, nicergolin, nimodipin, pyracetem, pyritinol and rivastigmin; for the main group of antidepressants: agomelatin, amitriptylin, amitriptylin oxide, bupropion, citapram, clomipramin, duloxetin, escitalopram, fluoxetin, fluvoxamin, maprotilin, mianserin, mirtazapin, nortriptylin, opipramol, paroxetin, reboxetin, sertralin, tranylcypromin, trazodon and trimipramin; for the main group of antidiabetics: acarbose, exenatid, glibenclamide, gliclacid, glimepirid, gliquidon, insulinaspart, insulinaspart biphasic, insulindetemir, insulinlargin, insulinglulisin, human insulin, human insulin-isophan biphasic, insulin-isophan, insulin-lispro, isophan-insulin, metformin, miglitol, nateglinid, pioglitazon, repaglinid, rosiglitazon, sitagliptin and vildagliptin; for the main group of antidotes: bis-sulfanyl propane sulfonic acid, deferasirox, deferoxamin, deferipron, dimercapto-propane sulfonic acid, dimethylaminophenol, disodium folinate, iron hexacyanoferrate, eserin, flumazenil, fomepizol, naloxone, sodium folinate, sodium thiosulfate, obidoxim chloride, pentetic acid, physostigmin, silbinin and tolonium chloride; for the main group of antiemetics or antivertigo agents: aprepitant, beta-histine, domperidon, flunarizin, fosaprepitant, granisetron, ondansetron, palonosetron and tropisetron; for the main group of antiepileptic agents: carbamazepin, clonazepam, diphenylhydantoin, phenytoin, dipropylacetic acid, valproic acid, ethosuximid, felbamat, gabapentin, potassium bromide, lacosamid, lamotrigin, levetiracetam, mesuximid, oxcarbazepin, phenobarbital, primidon, propylvalerianic acid, rufinamide, sultiam, tiagabin, topiramate, valproic acid, vigabatrin and zonisamide; for the main group of antiestrogens: clomife; for the main group of antihemorrhagics, antifibrinolytics and other hemostatic agents: aminomethylbenzoic acid, human blood clotting factor l, blood clotting factor Vlla, blood clotting factor Vll (CHO), recombinant blood clotting factor Vlll, human blood clotting factor Vlll, recombinant blood clotting factor lX, human blood clotting factor lX, blood clotting factor Xlll, eptacog alpha (activated), fibrinogen, gelatins, moroctocog alpha, nonacog alpha, octocog alpha (BHK), phytomenadione, human plasma proteins, human plasma proteins with factor VIII inhibitor bypass activity, proconvertin, protamine hydrochloride, tranexamic acid and troxerutin; for the main group of antihistamines: anazolin, azelastin, bamipin, cetirizin, chlorphenamine, chlorphenoxamine, cyproheptadine, desloratadine, dexchlorpheniramine, dimenhydrinate, dioxopromethazine, diphenhydramine, diphenylpyraline, ebastine, emedastine, epinastine, fexofenadine, hydroxyzine, levocabastine, levocetirizine, loratadine, rupatadine, terfenadine, tripelennamine and triprolidine; for the main group of antihypertonics: aliskiren, ambrisentan, amiloride+hydrochlorothiazide, hydrochlorothiazide+amiloride, bosentan, candesartan, captopril, clonidine, delapril, enalapril, enalaprilate, eprosartan, hydralazine, imidapril, indapamide, indoramine, lercanidipine, manidipine, methyldopa, minoxidil, moexipril, nilvadipin, nitrendipin, nitroprusside sodium, olmesartan, prazosin, reserpine, nitrogen monoxide, sitaxentan, telmisartan, terazosin, treprostinil and urapidil; for the main group of antihypoglycemics: diazoxide and glucagon; for the main group of antihypotonics: amezinium methyl sulfate, cafedrin, dopamine, etilefrin, levarterenol, norepinephrine, midodrin, noradrenaline, oxilofrin and theodrenaline; for the main group of anticoagulants: bivalirudin, certoparin sodium, dabigatran, dalteparin sodium, danaparoid sodium, drotrecogin alpha (activated), enoxaparin sodium, fondaparinux, heparin, heparin (low-molecular), nadroparin calcium, reviparin sodium, tinzaparin sodium, lepirudin, nadroparin calcium, pentosanpolysulfate sodium, protein C, reviparin sodium, rivaroxaban, tinzaparin sodium and warfarin; for the main group of antimycotics: amorolfin, amphotericin B, anidulafungin, bifonazole, caspofungin, ciclopirox, ciotrimazole, econazole, fenticonazole, fluconazole, flucytosin, griseofulvin, hexamidine, isoconazole, itraconazole, ketoconazole, micafungin, miconazole, naftifin, natamycin, nystatin, oxiconazole, posaconazole, sertaconazole, terbinafin, tioconazole, tolnaftat, undecylenic acid and voriconazole; for the main group of antineoplastic agents: alemtuzumab, alitretinoin, bevacizumab, arsenic trioxide, asparaginase, bexaroten, buserelin, celecoxib, cetuximab and colaspase; for the main group of antiparasitic agents: allethrin 1, acetic acid, permethrin and piperonylbutoxide; for the main group of antiphlogistics: aescin, ammonium bituminosulfonate, ammonium bituminosulfonate bright, benzydamine, bufexamac, cumarin, dimethylsulfoxide, guaiazulene, sodium bituminosulfonate and serrapeptase; for the main group of antipruriginosics: crotamiton, levomenthol, menthol and coal tar; for the main group of antipsoriatics: acitretin, dimethylfumarate and ethylhydrogenfumarate; for the main group of antipsychotics: aripiprazole; for the main group of antiseptics: ethacridin, ethanol, denatured ethanol, fenchon, glyoxal, hexetidin, hydroxyquinoline sulfate, potassium thiocyanate, methenamine-silver nitrate 1:2, phenoxyethanol, ionic silver and colloidal silver; for the main group of antiscabies agents: benzylbenzoate; for the main group of antitussives or expectorants: anethol, benproperin, cineol, codeine, dextromethorphan, dihydrocodeine, dropropizin, eucalyptol, guaifenesin, guajacol glycerine ether, levodropropizin, narcotin, noscapin, pentoxyverin, thymol and tyloxapol; for the main group of anticoagulants: argatroban; for the main group of anxiolytics: buspiron; for the main group of appetite curbing agents: amfepramon and cathine; for the main group of aromatase inhibitors: anastrozole, exemestan and letrozole; for the main group of arteriosclerosis agents: dodecyltetradecylhydroxypolyoxyethylene polyoxypropylene; for the main group of balneotherapeuticals and thermotherapy agents: humic acids; for the main group of β-lactam antibiotics: aztreonam, imipenem, cilastatin, doripenem, ertapenem, loracarbef, meropenem; for the main group of beta-receptor and calcium channel blockers and inhibitors of the renin-angiotensin-aldosterone system: acebutolol, atenolol, bisoprolol, betaxolol, bupranolol, carteolol, celiprolol, esmolol, fosinopril, gallopamil, irbesartan, levobunolol, lisinopril, losartan, metipranolol, metoprolol, nebivolol, nifedipine, nisoldipin, oxprenolol, penbutolol, perindopril, pindolol, propranolol, talinolol, valsartan and verapamil, for the main group of bisphosphonates: alendronate, alendronatic acid, clodronate, clodronic acid, etidronate and etidronic acid; for the main group of broadband penicillin: amoxicillin and ampicillin; for the main group of broadband penicillin+β-lactamase inhibitors: clavulanic acid and sulbactam; for the main group of bronchodilators: aminophyllin and bambuterol; for the main group of broncholytics or antiasthmatics: carbocisteine, ciclesonide, clenbuterol, fenoterol, formoterol, ipratropium bromide, ketotifen, montelukast, omalizumab, reproterol, salbutamol, salmeterol, terbutalin, theophyllin, theophyllin ethylene diamine, tiotropium bromide and tulobuterol; for the main group of calcium antagonists: amlodipin, diltiazem, felodipin and isradipin; for the main group of calcium replacement agents: calcium aminoethyl phosphate, calcium aspartate, calcium bis-(hydrogen aspartate), calcium chloride, calcium citrate, calcium gluconate, calcium hydrogen phosphate, calcium hydrogen phosphate, calcium lactobionate, calcium lactogluconate and calcium salts; for the main group of carboanhy[d]rase inhibitors: acetazolamide, binzolamide and dorzolamide; for the main group of cephalosporin: cefaclor, cefadroxil, cefalexin, cefazolin, cefepim, cefixim, cefotaxim, cefotiam, cefepodoxim, ceftazidim, ceftibuten, ceftriaxon, cefuroxim and ceph; for the main group of chemotherapy agents: co-trimoxazole, dapson, nifuratel, nitrofural, nitrofurantoin, nitrofurazon, nitroxolin, octenidin, pentamidin, ulfamethoxazole, taurolidin and trimethoprim; for the main group of cholagogues and bile duct therapeutic agents: menthon, α-pinene, β-pinene and ursodesoxycholic acid; for the main group of cholinergics: acetylcholine chloride, carbachol, distigmin bromide, neostigmin and pyridostigmin bromide; for the main group of corticoids: fludrocortisone for the main group of depot penicillin: benzylpenicillin-benzathin and benzylpenicillin-procaine; for the main group of dermatic agents: ammonium dodecylsulfate, betacarotene, DFMO, eflornithine, difluormethylornithine, dodecylbenzene sulfonic acid, nitrilotriethanol salt, ectoin, estradiol benzoate, ethyl linolate, framycetin, fusidinic acid, synthetic tannin, phenol-methanal-urea polycondensate sulfonated, urea, hexamethylene tetramine, hydroquinone, isotretinoin, potassium hydroxide, keratin, copper (II) nitrate, lithium succinate, methane thelinium bromide, methenamine, methoxypsoralene, mupirocin, nadifloxacin, pimecrolimus, podophyllotoxin, salicylic acid, nitric acid, selenium disulfide, sulfadiazine-silver, tacalcitol, tretinoin and tyrothricin; for the main group of disinfectants: aminopropyldodecylpropane diamine, cocospropylene diamine, dodecylpropane diamine, ethylene dioxydimethanol and triclosan; for the main group of disinfectants or antiseptics: aethacridin, aluminum acetate tartrate, amylmetacresol, bibrocathol, benzalkonium chloride, benzethonium chloride, benzyl alcohol, bishydroxymethyl urea, biphenyl-2-ol, bromchlorophen, cetylpyridinium chloride, 8-quinolinol sulfate, clioquinol, didecyldimethylammonium chloride, didecylmethyloxyethlammonium propionate, quinolinol sulfate potassium sulfate, chlorhexidin, chlorhydroxybenzoic acid, clorofen, cocospropylene diamine guanidinium acetate, dequalinium chloride, dibromhydroxybenzene sulfonic acid, dichlorbenzyl alcohol, dithranol, ethylhexanol, formaldehyde, glucoprotamine, glutaral, magnesium monoperoxyphthalate, mecetronium ethyl sulfate, oligodiiminoimidocarbonyliminohexamethylene, ortho-phthalaldehyde, peracetic acid, polyhexanid, povidone iodine, 1-propanol, 2-propanol, tetrahydrotetrakishydroxymethylimidazoimidazoldione, tosylchloramide sodium and hydrogen peroxide; for the main group of deodorants: chlorophyllin; for the main group of dietetics or nutritional supplements: methyloxobutyric acid, methyloxovalerianic acid (3), methyloxovalerianic acid (4) and oxophenylpropionic acid; for the main group of diagnostic agents and diagnosis preparation agents: aminolavulinic acid, aminolevulinic acid, 5-amino-4oxopentanoic acid, ceruletid, human corticorelin, iron oxide, ferumoxsil, fluorescein, gadobenic acid, gadobutrol, gadodiamide, gadofosveset, gadopentetic acid, gadoteridol, gadoteric acid, gadoxetic acid, galactose, 13C-urea, hexylaminooxopentanoate, indocyanine green, mangafodipir, palmitic acid, patent blue V, perflutren, polyvinyl chloride, protirelin, secretin, starch hydrolyzate, somatorelin, TRH and tuberculin purified for human use; for the main group of direct parasympathomimetics: bethanechol chloride; for the main group of diuretics: bumetanide, furosemide, piretanide, spironolactone, torasemide, triamterene, triamterene+hydrochlorothiazide and xipamide; for the main group of dopamine agonists: α-dihydroergocryptin; for the main group of circulation promoting agents: alprostadil, cinnarizin, moxaverin, naftidrofuryl, pentoxifyllin, prostaglandin E1 and xanthinol nicotinate; for the main group of iron replacement: ammonium iron sulfate; for the main group of emetics: apomorphine; for the main group of withdrawal agents/agents for treatment of addictive diseases: naltrexone, nicotine and vareniclin; for the main group of enzyme replacement therapy for Fabry's syndrome: agalsidase alpha and agalsidase beta; for the main group of enzyme inhibitors, enzyme deficiency products and transport proteines: carglumic acid, L-carnitine, levocarnitine, C1-esterase inhibitor, galsulfase, hyaluronidase, idursulfase, imiglucerase, laronidase and miglustat; for the main group of enzyme replacement therapy in Pompe's disease: alglucosidase alpha; for the main group of estrogens: estriol, conjugated estrogens and ethinylestradiol; for the main group of fibrinolytics: alteplase, reteplase, streptokinase, tenecteplase and urokinase; for the main group of film forming agents: carbomer and carmellose; for the main group of gallstone dissolvers: chenodesoxycholic acid; for the main group of gestagens: dienogest, drospirenone, dydrogesterone, gestodene, hydroxyprogesterone caproate, levonorgestrel, medrogestone, medroxyprogesterone, megestrolacetate, norelgestromin, norethisterone, norgestimate and D-norgestrel; for the main group of glaucoma treatment: bimatoprost and latanoprost; for the main group of geriatrics: potassium metabisulfite; for the main group of antipodagrics: probenecide; for the main group of glucocorticoids: alclometasone, amcinonide, beclometasone, betamethasone, budesonide, clobetasol, clobetasone, clocortolone, cloprednol, deflazacort, desoximetasone, dexamethasone, diflorasone, diflucortolone, flumetasone, flunisolide, fluocinolonacetonide, fluocinonide, fluocortolone, fluorometholone, fluprednidene, fluticasone, halometasone, hydrocortisone, hydrocortisone aceponate, hydrocortisone acetate, hydrocortisone-17-butyrate, hydrocortisone hydrogen succinate, methylprednisolone, mometasonfuroate, prednicarbate, prednisolone, prednisone, rimexolone, triamcinolone, triamcinolone acetonide, triamcinolone-16,21-diacetate and triamcinolone hexacetonide; for the main group of gonadorelin inhibitors: cetrorelix; for the main group of gynecologicals: gemeprost, copper, metergolin, methylergometrin, lactic acid, nonoxinol, progesterone, prostaglandin E2, quinagolide and sulprostone; for the main group of hemopoietic growth factors: becaplermin; for the main group of hemostyptics: cellulose oxidized regenerated, desmoressin and collagen; for the main group of hepatics: acetylmethionine, betaine dihydrogen citrate, choline hydrogen tartrate, potassium-iron-phosphate-citrate complex, ornithine aspartate and zinc acetate; for the main group of cardioglycosides (Digitalis lanata): β-acetyldigoxin, digitoxin and digoxin; for the main group of hyperemization agents: benzylnicotinate and isobornylacetate; for the main group of hypnotics or sedatives: brotizolam, chloralhydrate, clomethiazole, doxylamine, flunitrazepam, flurazepam, lormetazepam, melatonin, midazolam, nitrazepam, temazepam, zaleplon, zolpidem and zopiclon; for the main group of pituitary and hypothalamus hormones, other regulatory peptides and their inhibitors: carbetocin, choriogonadotropin alpha, choriongonadotropin, tetracosactid, β-1-24-corticotropin, follitropin alpha, follitropin beta, ganirelix, gonadorelin, gonadotrophinum chorionicum, gonadotrophinum hypophysicum, menotropin, lanreotid, LH-RH, lutropin alpha, mecaserim, nafarelin, octreotid, oxytocin, somatostatin, somatropin, terlipressin, thyrotrophin, urofollitropin, urogonatropin and human growth hormone; for the main group of immunomodulators: eculizumab, glatiramer, lenalidomide, lenograstim, palivizumab and pegvisomant; for the main group of immune stimulants: aldesleukin, dimepranolacedoben, filgrastim, inosine, interferon alpha-2a, interferon alpha-2b, interferon beta-1°, interferon beta-1b, interferon gamma-1b, pegfilgrastim, peginterferon alpha-2a and peginterferon alpha-2b; for the main group of immune suppressants: adalimumab, azathioprin, basiliximab, cyclosporin, cladribin, cyclosporin, daclizumab, efalizumab, everolimus, immunglobulin G rabbit antihuman-T-cell, infliximab, muromonab-CD3, mycophenolate mofetil, mycophenolic acid, natalizumab, sirolimus, tacrolimus and tocilizumab; for the main group of infusion and standard injection solutions or organ perfusion solutions: N-acetyltyrosine, gelatine polysuccinate, glucose, glutamine, glycerol dihydrogen phosphate, human albumen, potassium hydrogen glutamate, mannitol, sodium aminoethylhydrogen phosphate, sodium chloride, sodium hydrogen carbonate, oleic acid, 2-oxoglutaric acid, polyhydroxyethyl starch, hydrochloric acid, taurine, trometamol and xylitol; for the main group of inhaled narcotics: desfluran, dinitrogen monoxide and isofluran; for the main group of intestinal antiphlogistics: 5-aminosalicylic acid, mesalazin, (−)-α-bisabolol, levomenol, bromelain and choline stearate; for the main group of potassium replacement agents: potassium acetate, potassium chloride, potassium hydrogen aspartate, potassium hydrogen carbonate, potassium lactate and potassium malate; for the main group of potassium-sparing diuretics: amiloride; for the main group of capillary sealing agents: calcium dobesylate; for the main group of cardiacs: enoximon, icatibant, β-methyldigoxin, methyldigoxin, milrinon and oubain; for the main group of caries and parodontosis agents and other dental preparations: dectaflur, sodium fluoride and olaflur; for the main group of carminatives: dimethylpolysiloxane and dimethicone; for the main group of coronary drugs: ivabradin and molsidomine; for the main group of laxatives: bisacodyl, glycerine, glycerol, lactulose, macrogol, magnesium peroxide, sodium dioctylsulfosuccinate, sodium laurylsulfoacetate, sodium monohydrogen phosphate, sodium picosulfate, sodium sulfate, syrupy paraffin, polyethylene glycol and white vaseline oil paraffin; for the main group of photoprotective agents: actinoquinol; for the main group of lipid lowering drugs: atorvastatin, bezafibrate, colestyramine, cholestyramine, etofibrate, etofyllin clofibrate, ezetimib, fenofibrate, fluvastatin, gemfibrozil, lovastatin, magnesium pyridoxal phosphate glutamate, nicotinic acid, omega-3-acid ethyl ester, pravastatin and simvastatin; for the main group of topical anesthetics or neural therapeuticals: aethoform, p-aminobenzoic acid ethyl ester, articaine, benzocaine, bupivacaine, carticaine, chlorethane, cinchocaine, ethyl choride, felypressin, macrogol lauryl ether, mepivacaine, prilocaine, procaine, proxymetacaine, quinisocaine, ropivacaine and tetracaine; for the main group of gastrointestinal agents: hydrotalcit, lansoprazole, loperamide, methylnaltrexone bromide, metoclopramide, sodium alginate, olsalazin, omeprazole, oxetacaine, pancreas powder, pancreatin, pantoprazole, pepsin, pirenzepine, polymethylsiloxane, rabeprazole, racecadotril, ranitidine, silicon dioxide, simethicone, sucralfate, smectite, tannin-protein and tilactase; for the main group of magnesium replacement agents: magnesium chloride, magnesium salts and magnesium sulfate; for the main group of macrolide antibiotics: azithromycin, bacitracin, clarithromycin, daptomycin and erythromycin; for the main group of migraine agents: almotriptan, eletriptan, ergotamine, frovatriptan, naratriptan, rizatriptan, sumatriptan and zolmitriptan; for the main group of mineral preparations: calcium lactate, calcium saccharate, iron hydrogen aspartate, potassium aminoethylphosphate, potassium citrate, magnesium aminoethylphosphate, magnesium aspartate, magnesiumbis(hydrogenaspartate), magnesium citrate, magnesium gluconate, magnesium hydrogen citrate, magnesium hydrogen glutamate, magnesium hydrogen phosphate, magnesium orotate and magnesium oxide; for the main group of homocysteinuria treatment agents: betaine; for the main group of scleroderma and induratio penis plastica treatment agents: 4-aminobenzoic acid; for the main group of mucolytics: acetylcysteine; for the main group of mucolytics: desoxyribonuclease and dornase alpha; for the main group of muscle relaxants and reversers: alcuronium chloride, atracurium besylate, quinine, cisatracurium besylate, dantrolen, mivacurium chloride, orphenadrin, pancuronium bromide, pridinol, rocuronium bromide, succinyl choline chloride, suxamethonium chloride, sugammadex, tetrazepam, tizanidin, tolperison and vecuronium bromide; for the main group of myotonolytics: baclofen and methocarbamol; for the main group of narcosis agents: esketamine, etomidate, hydroxybutyiric acid, ketamine, propofol, remifentanil, sevofluran, sufentanil and thiopental-sodium; for the main group of neuroleptics: amisulpride, aaphenothiazine, pothipendyl, bnperidol, bomperidol, butyrophenone, chlorprothixen, clozapine, diphenylbutylpiperidine, droperidol, fluspirilen, pimozide, flupentixol, fluphenazine, levomepromazine and melperone; for the main group of neuropathy drugs and other neurotropic agents: cytidine phosphate, A-liponic acid, thioctic acid, pregabalin, riluzol and uridine phosphate; for the main group of nonsteroidal anti-inflammatory drugs: flurbiprofen, ketorolac-tromethanol, lomoxicam and parecoxib; for the main group of nonsteroidal antirheumatics: acecolfenac, aemetacin, alizapride, chloroquin, dexibuprofen, diclofenac, etofenamate, ibuprofen, indomethacin, ketoprofen, meloxicam, nabumeton, naproxen, phenylbutazone, piroxicam, proglumethacin and tiaprofenic acid; for the main group of ophthalmics: chondroitin sulfate, gramicidine, hydroxypropylguar, hydroxypropylmethylcellulose, hypromellose, inosine phosphate, lomefloxacin, methylhydroxypropylcellulose, naphazolin, nedrocromil, oxybuprocaine, pegaptanib, pilocarpin, polymyxin B, poly(vinylalcohol), povidone, ranibizumab, scopolamine, sulfacetamide, tafluprost, tetryzolin, timolol, travoprost, tropicamide, verteporfin and wool wax alcohols; for the main group of osteoporosis/calcium/bone metabolism regulators: alphacalcidol, calcitonin, disodium fluorophosphate, eptotermin alpha, hydroxycolecalciferol, ibandronate, ibandronic acid, pamidronate, pamidronic acid, human parathyroid hormone, paricalcitol, raloxifen, distrontium ranelate, risedronate, risedronic acid, teriparatid, tiludronate, tiludronic acid, zoledronate and zoledronic acid; for the main group of otologic agents: docusate-sodium; for the main group of parkinson drugs and other agents against extrapyramidal disturbances: benserazide, bromocriptine, budipine, cabergoline, carbidopa, entacapone, levodopa, lisuride, metixene, pergolide, piribedil, pramipexol, procyclidine, rasagiline, ropinirole, rotigotine, selegiline, tetrabenazine, tiapride, tolcapone and trihexypenidyl; for the main group of penicillins: benzylpenicillin and dicloxacillin; for the main group of phosphate binders: algeldrate, hydrated aluminum oxide, calcium acetate and calcium carbonate; for the main group of phosphate replacement agents: sodium glycerophosphate; for the main group of photosensitizers: ammoidine and methoxsalene; for the main group of polyaromatic retinoids: adapalene; for the main group of progestagenics: desogestrel and etonogestrel; for the main group of protease inhibitors: atazanavir and lopinavir; for the main group of proteinase inhibitors: antithrombin lll; for the main group of protozoan agents: artemether and lumefantrine; for the main group of psychoanaleptics: atomoxetin, metamfepramon and methylphenidate; for the main group of psychoenergetics: deanol; for the main group of psychopharmaceuticals: doxepin, haloperidol, imipramine, lithium salts, lorazepam, medazepam, memantin, moclobemide, modafinil, olanzapine, oxazepam, paliperidone, perazine, perphenazine, phenothiazines, pimozide, pipamperone, prazepam, promethazine, prothipendyl, quetiapine, risperidone, sertindole, sulpirid, thioridazine, thioxanthene, venlafaxine, ziprasidone, zotepine and zuclopenthixol; for the main group of rhinologics or sinusitis agents: Emser salt, synthetic Emser salt, natural sea salt, oxymetazolin, silver-protein acetyl tannate, tramazoline, xanthan gum and xylometazoline; for the main group of roborants or tonics: iron (III) citrate and glutaminic acid; for the main group of X-ray contrast agents: amidotrizoic acid, barium sulfate, diatrizoate, iobitridol, iodixanol, iohexol, iomeprol, iopamidol, iopromide iosarcol, iotrolan, iotroxic acid, ioxaglic acid and ioxitalamic acid; for the main group of saluretics: bemetizide, bendroflumethiazide, chlorthalidone, clopamide, hydrochlorothiazide, hydrochlorothiazide+amiloride, hydrochlorothiazide+triamterene and mefruside; for the main group of thyroid therapeutic agents: cinacalcet, potassium iodide, levothyroxin, liothyronin, sodium iodide, sodium perchlorate, propylthiouracil, thiouracils and L-thyroxin; for the main group of essential amino acids: histidine, isoleucine, leucine, lysine, phenylalanine, threonine, tryptophan, tyrosine and valine; for the main group of secretolytics: ambroxol and bromhexine; for the main group of serums, immunglobulins and inoculants: immunglobulin (anti-D), immunglobulin (botulismus), immunglobulin (cytomegalia), immunglobulin (hepatitis B), immunglobulin (human), immunglobulin (tetanus), immunglobulin (rabies) and immunglobulin (varicella-zoster); for the main group of sexual hormones and their inhibitors: estradiol, estradiol valerate, mestranol, mifepristone, prasterone, testosterone and tibolone; for the main group of spasmolytics or anticholinergics: atropine, atropine sulfate, biperiden, bornaprine, borneol, butylscopolaminium bromide, camphen, cyclopentolate, darfenacin, glycopyrronium bromide, hymecromone, hyoscine butylbromide, mebeverine and pipenzolate bromide; for the main group of trace elements: bis(L-histidinato)zinc, chromium chloride, chromium hydrogen aspartate, cobalt hydrogen aspartate, iron (III) chloride, copper (II) chloride, copper (II) hydrogen aspartate, manganese (II) chloride, manganese (II) hydrogen aspartate, sodium molybdate, sodium selenite, zinc aspartate, zinc bishydrogen aspartate, zinc chloride, zinc gluconate, zinc histidine, zinc orotate and zinc sulfate; for the main group of replacement agents: disodium hydrogen citrate, magnesium acetate, sodium acetate, sodium hydroxide and sodium lactate; for the main group of sympathomimetics: dipivefrin and ephedrine; for the main group of tetracyclines: chlortetracycline, demeclocycline, doxycycline, meclocycline, minocycline, oxytetracycline and tetracycline; for the main group of platelet clotting inhibitors: abciximab, cilostazol, clopidogrel, eptifibatide, iloprost, ticlopidine and tirofiban; for the main group of thyreostatics: carbimazole, methimazole and thiamazole; for the main group of tocolytics: atosiban; for the main group of toxoplasmosis, pneumocystis carinii and pneumonia drugs: atovaquone; for the main group of tranquilizers (benzodiazepin): alprazolam, bromazepam, chlordiazepoxide, clobazam, diazepam and dipotassium clorazepate; for the main group of tuberculosis drugs: aminosalicylic acid, ethambutol, isoniazide, protionamide, pyrazinamide, rifampicin and terizidone; for the main group of ulcer therapeuticals: bismuth nitrate, bismuth tetraoxodialuminate, cimetidine, esomeprazole and famotidine; for the main group of uricostatics: allopurinol and benzbromarone; for the main group of urologicals: dutasteride, fesoterodine, finasteride, flavoxate, potassium aminobenzoate, potassium sodium hydrogen citrate, lanthanum (III) carbonate, mercaptamine, methionine, oxybutynine, phenoxybenzamine, phytosterol, polystyrene divinylbe[n]zene sulfonic acid, polystyrene sulfonic acid, propiverine, propyl-4-hydroxybenzoate, sevelamer, solifenacin, tamsulosin, tiopronin, tolterodine, trospium chloride and yohimbin; for the main group of uterus agents: dinoprostone; for the main group of vasodilators: adenosine, buflomedil, carvedilol, codergocrin, dihydralazine, dihydroergotoxin, dipyridamol, glycerol trinitrate, isosorbide dinitrate, isosorbide mononitrate, nitroglycerin, pentaerythrityl tetranitrate, sildenafil, tadalafil, trapidil and vardenafil; for the main group of venous therapeuticals: heparinoids, mucopolysaccharide polysulfuric acid esters, oligo (O-sulfo)rutoside, polidocanole, rutin and rutoside; for the main group of vein tonic agents: diosmin; for the main group of virustatics: abacavir, aciclovir, adefovir, amantadine, brivudin, cidofovir, darunavir, didanosine, efavirenz, emtricitabine, entecavir, etravirine, famciclovir, fosamprenavir, ganciclovir, idoxuridine, imiquimod, indinavir, interferon beta, lamivudine, maraviroc, nelfinavir, nevirapine, oseltamivir, raltegravir, ribavirin, ritonavir, saquinavir, stavudine, telbivudine, tenofovir, tipranavir, trifluridine, tromantadine, valaciclovir, valganciclovir, zanamivir and zidovudine; for the main group of vitamins: aneurin, ascorbic acid, benfotiamine, biotin, calcifediol, ergocalciferol, calciferol, calcipotriol, calcitriol, calcium pantothenate, colecalciferol, cyanocobalamine, dihydrotachysterol, hydroxocobalamine, purified silicon dioxide, sodium ascorbate, sodium pantothenate, nicotinamide, nicotinic acid amide, pyridoxin, retinol, riboflavin, thiamine, thiamine dihydrogen phosphate-dihydrogen phosphate (ester salt), thiamine disulfide, thiamine nitrate, α-tocopherol, RRR-α-tocopherol, α-tocopherol acetate, RRR-α-tocopherol acetate, DL-α-tocopherol hydrogen succinate, RRR-α-tocopherol hydrogen succinate, vitamin A, vitamin-A-acid, vitamin $B_1$, vitamin $B_2$, vitamin $B_6$, vitamin $B_{12}$, vitamin C, vitamin $D_2$, vitamin $D_3$, vitamin E and vitamin $K_1$; for the main group of wound and scar treatment agents: allantoin, calcium alginate, dexpanthenol, ethylcyanoacrylate, lactide-caprolactone copolymers, poly(butylmethacrylate-co-methylmethacrylate) (x:y), polyurethane and titanium dioxide; for the main group of urine acidification agents: ammonium chloride; for the main group of cytoreductive agents: anagrelid; for the main group of cytostatics, other antineoplastic agents and protectives: adriamycin, amethopterin, bendamustine, bleomycin, bortezomb, busulfan, capecitabine, carboplatin, CCNU, lomustine, chlorambucil, cisplatin, cyclophosphamide, cytarabine, dacarbazine, dasatinib, daunorubicin, dexrazoxan, docetaxel, doxorubicin, epirubicin, erlotinib, estramustine, etoposide, fludarabine, fluorouracil, flutamide, 5-FU, fulvestrant, gemcitabine, goserelin, hydroxycarbamide, ibritumomabtiuxetan, idarubicin, ifosfamide, imatinib, irinotecan, lapatinib, leuprorelin, melphalan, mercaptopurine, mesna, methotrexate, methylaminooxopentanoate, miltefosine, mitomycin, mitotane, mitoxantrone, nelarabine, nilotinib, nimustin, oxaliplatin, paclitaxel, palifermin, panitumumab, pegaspargase, pemetrexed, porfimer-sodium, procarbazine, rasburicase, rituximab, sorafenib, sunitinib, tamoxifen, tegafur, temoporfin, temozolomide, temsirolimus, thiotepa, thioguanine, topotecan, toremifene, trabectedine, trastuzumab, treosulfan, triptorelin, trofosfamide, uracil, vinblastin, vincristin, vindesine and vinorelbine; for the main group of biomaterials or medical plastics or various materials: hydroxylapatite, methylmethacrylate, poly(methylacrylate-co-methylmethacrylate) (x:y), tricalcium bisphosphate and zirconium (IV) oxide as special active substance or active substance mixture.

An especially suitable embodiment of the composition according to the invention proposes that this embodiment of the invented composition has, as active ingredient, an analgesic, especially an analgesic that is chosen from the above indicated special analgesics, and the content of this analgesic in the liquid composition that is mechanically foamed is varied in particular between 0.1 wt. % and 20 wt. %, preferably in a concentration between 2 wt. % and 10 wt. %.

If the composition of the invention is to be used as foam for treatment of fungal infections, then it may include, as pharmaceutical active ingredient, at least one antimycotic, especially an antimycotic that is chosen from the above indicated special antimycotics. Preferably this antimycotic is chosen from the group comprising chlotrimazol, biphonazol, econazol, phenticonazol, isoconazol, oxyconazol, sertaconazol, thioconazol, terbinafin, myconazol, ketoconazol, itraconazol, fluconazol, voriconazol, as well as derivates of the aforementioned substances.

In particular, the concentration of an antimycotic active substance varies between 0.01 wt. % and 10 wt. %, especially between 0.2 wt. % and 5 wt. %, in terms of the liquid composition that is exclusively mechanically foamed during application. A foam produced in exclusively mechanical fashion from such a liquid composition during its application can then be used in particular with a very high pharmaceutical efficacy for nail and foot fungal infections and for saccharomycete infections, the high pharmaceutical efficacy being manifested in that these fungal infections are curtailed already after a few applications and also healed in a short time after the application is repeated.

Another embodiment of the composition according to the invention includes as an active ingredient, at least one corticoid active ingredient, especially a corticoid active ingredient that is chosen from the above indicated special corticoid active ingredients, wherein the corticoid active ingredient is chosen from the group consisting of glucocorticoids, mineral corticoids and derivates of these. Depending on the particular corticoid active ingredient contained in the composition of the invention, the concentration of this corticoid active ingredient varies between 0.001 wt. % and 3 wt. %, preferably between 0.1 wt. % and 0.8 wt. %.

Preferred glucocorticoids are chosen from the group consisting of clobetasol-17-propionate, diflucortolone-21-valerate, amcinonide, betamethasone-17,21-dipropionate, betamethasone-17-valerate, desocimethasone, diflucortolone-21-valerate, fluocinolone acetonide, fluocinonide, fluocortolone, fluprednidene-21-acetate, fluthicasone-17-propionate, halcinonide, hydrocortisone-21-acetate-17-propionate, hydrocortisone-17-butyrate-21-propionate, hydrocortisone-17-butyrate, methylpredisolonaceponate, momethasone, momethasone furoate, prednicarbate, triamcinolonacetonide, clobethasone butyrate, clocortolone-21-pivalate, fluocortinbutyl, flumethasone-21-pivalate, hydrocortisone and derivates of the aforementioned substances.

Another embodiment of the composition according to the invention proposes that the composition of the invention contain, as active ingredient, at least one topical anesthetic, especially a topical anesthetic that is chosen from the above indicated special topical anesthetics, and the concentration of this topical anesthetic, depending on the particular active ingredient, varies in particular between 3 wt. % and 15 wt. %, especially between 6 wt. % and 12 wt. %, in terms of the concentration of active ingredient in the liquid composition.

Especially preferred topical anesthetics are chosen from the group consisting of benzocaine, procaine, tetracaine, lidocaine, etidocaine, prilocaine, mepivacaine, bupivacaine, S-ropivacaine, articaine and their derivates.

Another embodiment of the composition according to the invention calls for the composition to contain at least one immunomodulator in a concentration between 0.03 wt. % and 0.1 wt. %, and the above indicated special immunomodulators are especially preferred.

An especially suitable modification of the composition of the invention comprises, as an active ingredient or mixture of active ingredients, a nonopioid analgesic/antiphlogistic agent, especially a non-opioid analgesic/antiphlogistic that is chosen from the above indicated special non-opioid analgesics/antiphlogictics. These include in particular the salicylates, preferably acetylsalicylic acid and/or diflunisal, acetic acid derivates such as indomethacin, acemethacin, diclofenac and/or lonazolac, propionic acid derivates such as ibuprofen, flurbiprofen, ketoprofen, dexketoprofen, dexibuprofen, tarenflurbil, nimesulide, naproxen and/or thiaprofen acid, oxicams, such as pyroxicam, tenoxicam, meloxicam and/or lornoxicam, anthranylic acid derivates such as mefenaminic acid and/or flufenaminic acid, aniline derivates such as paracetamol, and 1-phenyl-2,3-dimethyl-3-pyrazolin-5-one derivates, such as phenazone, propyphenazone and/or metamizol, their salts and their derivates.

Depending on the particular application of the above-described embodiments of the composition of the invention, the concentration of the analgesic/antiphlogistic active substance in the liquid composition will vary between 0.5 wt. % and 8 wt. %, especially between 1 wt. % and 5 wt. %.

Of course, it is also possible for the composition of the invention to include, as active ingredient, a mixture of active ingredients, as long as this mixture of ingredients is mutually compatible. Such embodiments of the composition of the invention will be used for treating generally milder skin ailments, such as milder forms of eczema, acne, lichen, insect bites, mycoses and/or treatments of surface wounds with the foam created from the composition of the invention, in which case the active ingredient or mixture of active ingredients is chosen from the group containing terbinafin, clobethasone butyrate, erythromycin, benzocaine, dexamethasone, calcipotriol, tretinoin, minoxidil, bifonazole, dexpanthenol, salicylic acid, prednicarbate, momethasone furoate.

It should be clarified that all concentration figures indicated in this specification refer each time to the liquid composition prior to its foaming, unless otherwise expressly indicated.

An especially suitable embodiment of the composition of the invention includes, as the phospholipid foaming agent, a phosphatidyl choline isolated from soy beans, and in particular the concentration of this phosphatidyl choline in the phospholipid foaming agent is more than 50 wt. %, preferably between 50 wt. % and 95 wt. %, in relation to the dry substance of the phospholipid foaming agent. Especially when this phospholipid foaming agent contains at most 15 wt. % of lyso-phosphatidyl choline, at most 10 wt. % of phosphatidic acid and at most 10 wt. % of phosphatidyl ethanolamine, one can create a foam with this special foaming agent that can be diversely adapted to the particular requirements of the application site by varying its concentration.

Furthermore, in some embodiments, it may be important for the aforementioned special foaming agent that the phosphatidyl choline contained in the phospholipid foaming agent have an acid number of at most 10, a peroxide number of at most 10, and an oil concentration of at most 6 wt. % in terms of the dry substance of this phospholipid foaming agent, the liquid composition forming the basis of the foam has an especially long shelf life, without requiring a higher concentration of antioxidants or stabilizers, especially for the aforementioned phospholipid foaming agent.

The concentration of the phospholipid foaming agent contained in the liquid composition, in some embodiments, should be such that the foams mentioned at the outset for the method of the invention and for the composition of the invention and specified by the foam volume and by the foam stability can be created. Preferably, a liquid composition which is purely mechanically foamed has the phospholipid foaming agent in a concentration between 2 wt. % and 25 wt. %, especially in a concentration between 4 wt. % and 15 wt. %.

The general remarks given above on the method of the invention also hold for the composition of the invention, wherein the composition of the invention contains, besides water, preferably an alcohol and especially propylene glycol, whose concentration, depending on the desired and above-specified foam, varies between 2 wt. % and 25 wt. %, especially between 5 wt. % and 15 wt. %.

As regards the pH value, it is stipulated that especially the liquid composition of the invention has a pH value that is skin-tolerated and, depending on the particular site of application, lies between 4.8 and 8.8. In order to assure the above-indicated pH value, it is especially advantageous to add to the composition of the invention at least one buffer, especially sodium dihydrogen phosphate dihydrate and/or disodium hydrogen phosphate dodecahydrate.

The composition of the invention as described in detail above can be foamed with any suitable foam applicator, e.g., the applicators made by Rexam/Airspray (rexamairspray dot corn, and made and marketed under the name M3 mini foamer or those of made by Calmar/MeadWestvaco (Keltec), and also disclosed in EP 0 565 713 and EP 0 613 728, hereby incorporated by reference, and where further technical details about these foam applicators will be found. Thus, in particular, the present invention contemplates a foam applicator that includes a composition of the invention as described in detail above.

Moreover, the present invention relates to methods for treatment of the following illnesses.

In one embodiment, a method is contemplated that includes the treatment of atopic eczema or neurodermitis, wherein the treatment method of the invention involves the applying of a foam containing an immunomodulator, as is produced in particular from the previously described composition of the invention, to the skin of a warm-blooded mammal in need thereof. In particular, tacrolimus is chosen as the immunomodulator. Depending on the particular immunomodulator chosen, its concentration will vary preferably between 0.03 wt. % and 0.1 wt. %.

In one embodiment, a method is contemplated for the treatment of inflammatory or pruritic skin ailments, psoriasis, dermatitis, neurodermitis or psoriasis in a patient in need thereof, comprising the application of a foam containing a glucocorticoid, as is produced e.g, in particular from described compositions, to the skin of a warm-blooded mammal. In particular, the glucocorticoid in this treatment method is chosen from the group consisting of betamethasone, dexamethasone, predincarbate, mometasone furoate and clobetasone butyrate. Depending on the glucocorticoid, its concentration varies between 0.01 wt. % and 0.4 wt. %.

In one embodiment, a method is contemplated for the treatment of of pain, inflammation, rheumatic ailments or acute trauma in a patient in need thereof and comprises the application of a foam containing an analgesic, as is produced in particular from the previously described composition of the invention, to the skin of a warm-blooded mammal. Preferably, the analgesic in this treatment method is chosen from the group consisting of diclofenac, ketoprofen and ibuprofen. Depending on the analgesic, its concentration varies between 0.5 wt. % and 10 wt. %.

In one embodiment, a method is contemplated for the treatment of of mycotic infections comprises the application of a foam containing an antimycotic, as is produced in particular from the previously described composition of the invention, to the skin or nails of a warm-blooded mammal in need thereof. Preferably in this treatment method the antimycotic is chosen from the group comprising bifonazole and terbinafin. Depending on the antimycotic, its concentration varies between 0.1 wt. % and 20 wt. %, preferably between 2 wt. % and 10 wt. %.

In one embodiment, a method is contemplated for the treatment of infections with Gram positive microbes, anaerobic microbes and mycoplasma, especially for treatment of acne, in a patient in need thereof, and comprises the application of a foam containing an antibiotic, as is produced in particular from the previously described composition of the invention, to the skin of a warm-blooded mammal. Preferably in this treatment method the antibiotic chosen is erythromycin, especially in a concentration between 2 wt. % and 4 wt. %.

In one embodiment, a method is contemplated for the treatment of itching of the skin comprises the application of a foam containing a topical anesthetic, as is produced in particular from the previously described composition of the invention, to the skin of a warm-blooded mammal. Preferably in this treatment method the topical anesthetic chosen is benzocaine and/or lidocaine, especially in a concentration between 1 wt. % and 20 wt. %, preferably 2 wt. % and 10 wt. %.

In one embodiment, a method is contemplated for the treatment of psoriasis and comprises the application of a foam containing calcipotriol, as is produced in particular from the previously described composition of the invention, to the skin of a warm-blooded mammal in need thereof. Preferably the calcipotriol in this treatment method is provided in a concentration between 0.005 wt. % and 0.05 wt. %.

In one embodiment, a method is contemplated for the treatment of acne, especially acne comedonica and acne papulopustulosa, comprises the application of a foam containing tretinoin, as is produced in particular from the previously described composition of the invention, to the skin of a warm-blooded mammal in need thereof. Preferably in this treatment method the tretinoin is provided in a concentration between 0.05 wt. % and 0.1 wt. %.

In one embodiment, a method is contemplated for treatment of hair loss comprises the application of a foam containing minoxidil, as is produced in particular from the previously described composition of the invention, to the skin of a warm-blooded mammal in need thereof. Preferably in this treatment method the minoxidil is provided in a concentration between 38 wt. % and 6 wt. %.

In one embodiment, a method is contemplated for the antiseptic treatment of superficial wounds comprises the application of a disclosed foam that may include an antimycotic to a patient in need thereof. Preferably in this treatment method comprises the application of foam as is produced in particular from the previously described composition of the invention, to the wound of a warm-blooded mammal. Preferably in this treatment method the dexpanthenol is provided in a concentration between 0.03 wt. % and 1 wt. %.

In one embodiment, a method is contemplated for the treatment of herpes and the side effects accompanying herpes in a patient need thereof and comprises the application of a foam containing aciclovir, as is produced in particular from the previously described composition of the invention, to the skin of a warm-blooded mammal. Preferably in this treatment method the aciclovir is provided in a concentration between 3 wt. % and 7 wt. %.

In one embodiment, a method is contemplated for the treatment of mild to medium severe psoriasis of the scalp in a patient in need thereof and comprises the application of a foam containing salicylic acid, as is produced in particular from the previously described composition of the invention, to the scalp of a warm-blooded mammal. Preferably in this treatment method the salicylic acid is provided in a concentration between 8 wt. % and 12 wt. %.

In the above description of the different embodiments of the method of treatment of the invention the term application is used in the singular. However, this should also refer to the repeated application, at intervals of time, within a given period, especially within 24 hours.

Likewise, the term skin used throughout the text covers not only the particular ailing regions of the skin, but also all surfaces of the human or animal body accessible to the application of the foam produced from the composition of the invention, and thus in particular, besides the skin or scalp itself, also nails, hair, teeth, hooves or the mucosa in mouth, nose, vagina or foreskin, the regions of the ear and especially the inner ear, the region of the anus and the colon, the region of the eyes, especially the region under the eyelid, such as conjunctiva, cornea and lacrial sac, while the term mammal comprises animals and humans.

For clarity, and to avoid repetition, it is pointed out that the remarks, details and benefits described at the outset in connection with the method of the invention also apply accordingly for the composition of the invention and also the above described treatment procedure of the invention, as do the remarks, details and benefits described in connection with the composition of the invention for the method of the invention and the treatment procedure of the invention.

The present invention shall be further described hereafter by means of the following Examples.

EXAMPLES

Description of the SITA Measurement Method

Figure 2:
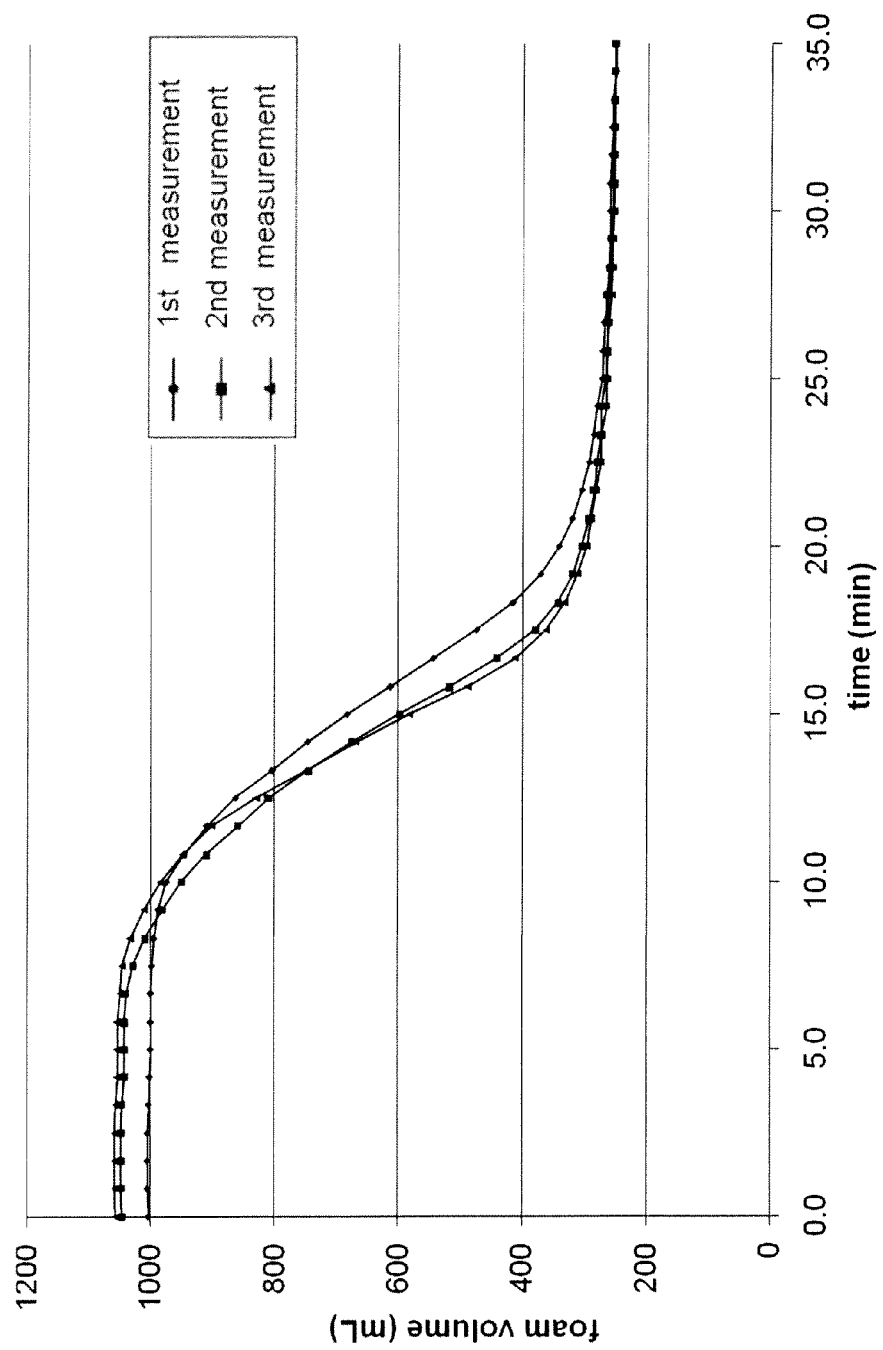
Figure 3:
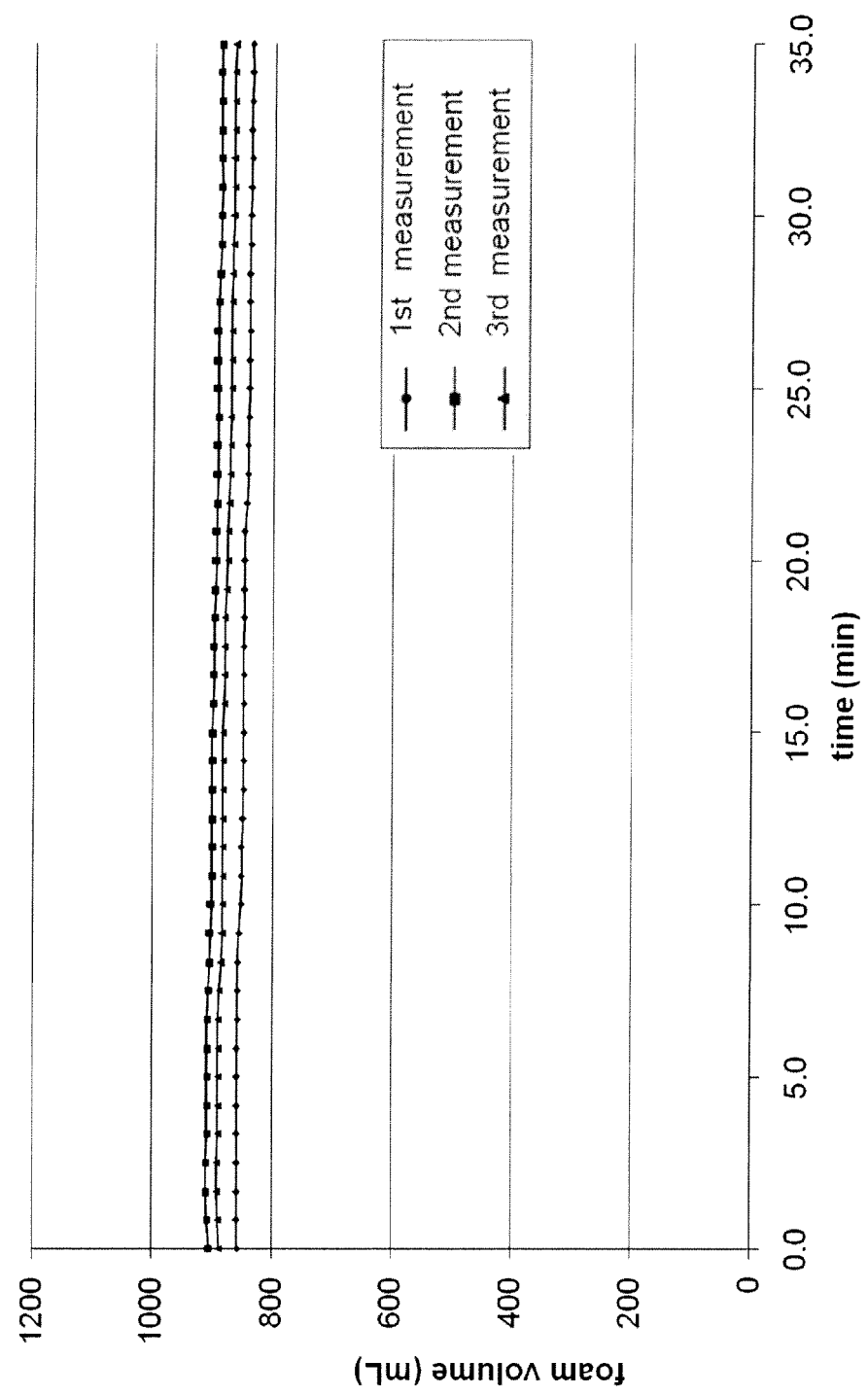

For the determination of the foam volume and the foam stability, a "SITA foam tester R-2000" (manufactured by SITA Messtechnik GmbH, Dresden) was used, as is described in detail in EP 1 092 970. This measurement device was provided with a rotor as shown in FIGS. 2 and 3 of DE 197 40 0095 and also described there. This rotor consists of a stirring shaft and a circular disk oriented perpendicular to this, with a diameter of 70 mm, above and below the circular disk there being provided four symmetrical stirring blades, oriented at right angles to each other. Each stirring blade has a rectangular base surface of 23 mm×12 mm. In cross section, each stirring blade has the shape of a triangle, with a height of 5 mm, so that each stirring surface accordingly forms a roof with a ridge angle of 90 degrees. The stirring blades each consist of a Conidur fine perforated plate (manufactured by HeinLehmann, Krefeld) and have a plate thickness of 0.5 mm, a perforation of 0.5 and a spacing of 3.2.

In all measurements, the sample volume was 250 ml, being automatically withdrawn by the measuring device from the reservoir tank, filled with at least 300 ml of sample. The sample was placed carefully into the reservoir tank, avoiding any foam formation if possible. After a waiting time of ten minutes, so that any air bubbles formed during the filling could migrate to the surface and thus not falsify the volume, 250 ml of the sample being investigated was drawn into the measuring space and measured.

With a rotor speed of 2000 rpm, the sample being measured in the measuring space was subjected to five rotor cycles of 20 seconds each to create the foam. Between rotor cycles there was a pause of around 15 seconds.

By means of the sensors described in DE 199 49 922, which automatically and continuously scanned the foam surface, the foam volume was measured immediately after the five rotor cycles were completed. The foam stability was automatically detected by the instrument over a period of 35 minutes in total for which the foam volume was measured every 50 seconds by means of the needle detectors. The volume values so obtained were recorded directly by dedicated software and hardware of the instrument.

The control system of the SITA foam tester is such that, after the measurement space is filled with 250 ml of sample, the needle detectors travel only as far as the surface of the sample and, accordingly, place the zero point for the foam volume on the surface of the measurement sample and not on the floor of the measurement space. After elapsing of the aforementioned rotor cycles for foaming the particular sample, there sometimes remained in the measurement space a liquid phase of the sample, depending on the composition of the particular sample being investigated, so that the volume of this liquid phase was also detected in the above described measurement according to the particular measurement value of the foam volume and is defined accordingly as foam volume in the sense of the present specification, while the time change in this foam volume is the foam stability. In other words, this means that, depending on the particular sample measured, the foam volume consists not only of the volume of the actual foam, but also of the volume of nonfoamed liquid sample remaining in the measurement space.

The following charts 1 to 17 plot all three measurement values for the particular composition, so that the reproducibility of the measurement method can be seen quite well from this.

All the following sample embodiments in which diclofenac is indicated as the active substance have this active substance in the form of the sodium salt of diclofenac, i.e., diclofenac-sodium.

Examples 1 to 5

Following the customary procedure, a composition containing ketoprofen, one containing lidocaine hydrochloride, one containing prednicarbate, one containing diclofenac and one containing clotrimazol were prepared, having the following ingredients:

| | Ingredient | Composition in wt. % |
|---|---|---|
| 1 | Ketoprofen | 10.00 |
| 2 | Propylene glycol | 10.00 |
| 3 | 2-Propanol | 8.00 |
| 4 | Phospholipid foaming agent A | 10.00 |
| 5 | Sodium hydrogen phosphate dihydrate | 0.25 |
| 6 | Disodium hydrogen phosphate dodecahydrate, cryst. | 0.57 |
| 7 | Sodium hydroxide | 1.55 |
| 8 | Peppermint oil | 0.15 |
| 9 | Ultrapure water | 59.48 |
| | TOTAL | 100.00 |

The foam behavior of this composition 1 is shown in FIG. 1.

| | Ingredient | Composition in wt. % |
|---|---|---|
| 1 | Lidocaine hydrochloride | 10.00 |
| 2 | Propylene glycol | 10.00 |
| 3 | 2-Propanol | 11.00 |
| 4 | Phospholipid foaming agent A | 10.00 |
| 5 | Sodium dihydrogen phosphate dihydrate | 0.12 |
| 6 | Disodium hydrogen phosphate dodecahydrate, cryst. | 0.66 |
| 7 | Sodium hydroxide 20% w/w | 4.00 |
| 8 | Peppermint oil | 0.15 |
| 9 | Ultrapure water | 54.07 |
| | TOTAL | 100.00 |

The foam behavior of this composition 2 is shown in FIG. 2.

| | Ingredient | Composition in wt. % |
|---|---|---|
| 1 | Prednicarbate | 0.10 |
| 2 | Propylene glycol | 15.00 |
| 3 | 2-Propanol | 9.35 |
| 4 | Phospholipid foaming agent B | 5.00 |
| 5 | Sodium dihydrogen phosphate dihydrate | 0.50 |
| 6 | Disodium hydrogen phosphate dodecahydrate, cryst. | 1.14 |
| 7 | Sodium hydroxide 10% w/w | 1.00 |
| 8 | Tegosoft GC | 8.60 |
| 9 | Ultrapure water | 59.31 |
| | TOTAL | 100.00 |

The foam behavior of this composition 3 is shown in FIG. 3.

| | Ingredient | Composition in wt. % |
|---|---|---|
| 1 | Diclofenac | 4.000 |
| 2 | 1,2-propane diol | 15.000 |
| 3 | 2-Propanol | 10.250 |
| 4 | L (+) ascorbylpalmitate | 0.020 |
| 5 | Phospholipid foaming agent A | 20.000 |
| 6 | Sodium dihydrogen phosphate, ultrapure | 0.120 |
| 7 | Disodium hydrogen phosphate dodecahydrate, ultrapure | 0.660 |
| 8 | EDTA, Titriplex III | 0.040 |
| 9 | Ultrapure water | 49.710 |
| 10 | Peppermint oil | 0.200 |
| | TOTAL | 100.00 |

Figure 4:
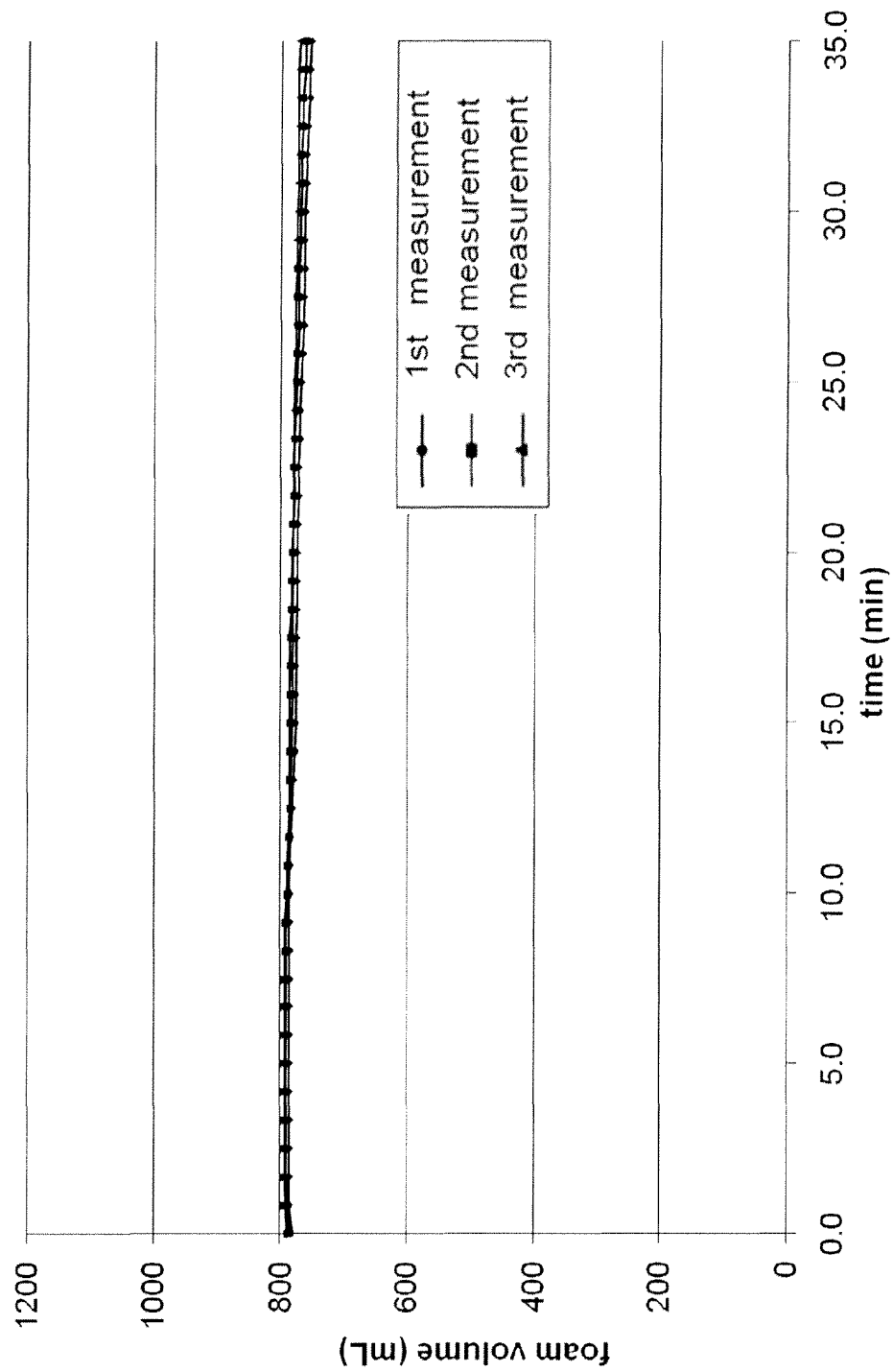

The foam behavior of this composition 4 is shown in FIG. 4.

| | Ingredient | Composition in wt. % |
|---|---|---|
| 1 | Clotrimazol | 0.5 |
| 2 | Propylene glycol | 20.00 |
| 3 | 2-Propanol | 8.00 |
| 4 | Phospholipid foaming agent A | 8.00 |
| 5 | Sodium dihydrogen phosphate dihydrate | 0.12 |
| 6 | Disodium hydrogen phosphate dodecahydrate, cryst. | 0.66 |
| 7 | Sodium hydroxide 20% w/w | 1.00 |
| 8 | Peppermint oil | 0.20 |
| 9 | Polysorbate 80 | 13.00 |
| 10 | Ultrapure water | 48.52 |
| | TOTAL | 100.00 |

Figure 5:
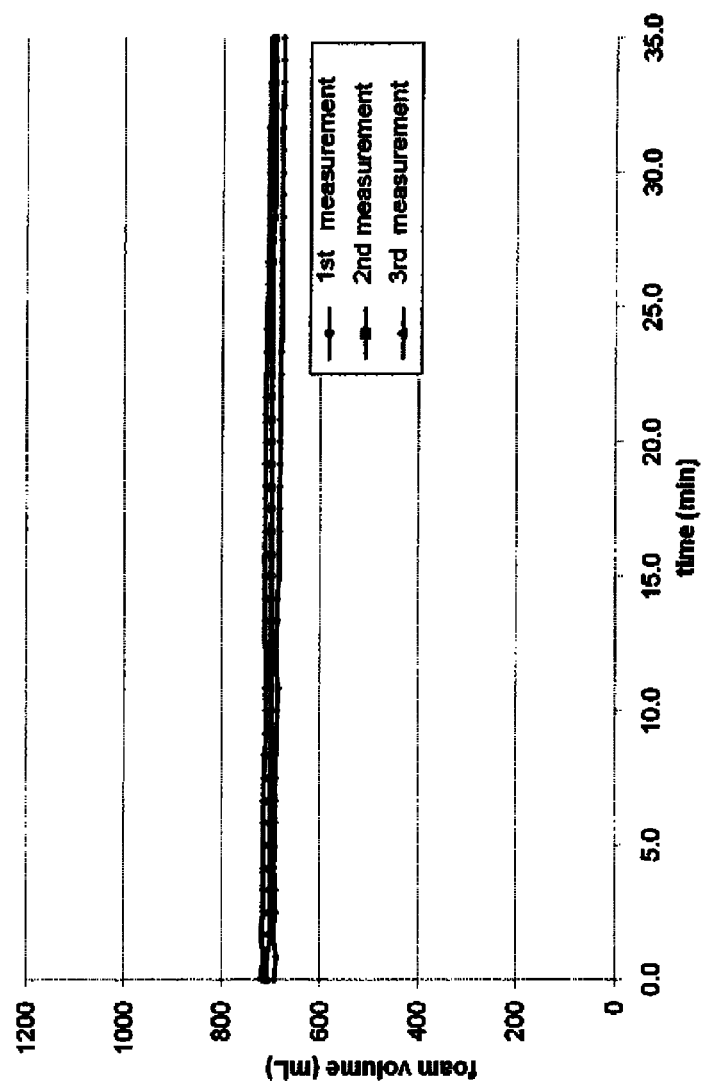

The foam behavior of this composition 5 is shown in FIG. 5.

Twenty subjects (11 female, 9 male) suffering from fungal disease between the toes and also partly on the toe nails had the fungally attacked regions of the left foot treated twice daily with a foam prepared by the above-described SITA measurement method. The treatment was done in that the ailing area was covered with a foam layer around 0.5 to 1 cm thick and then this foam was manually rubbed in. The total treatment time lasted up to 14 days.

The ailing area of the right foot was treated with a composition 5, identical in ingredients, while this composition 5 was foamed by means of a "M3 mini foamer" from Rexam/Airspray immediately prior to application.

Regardless of which foam had been applied to the ailing areas, 16 subjects reported a direct decrease in itching already after the first application of the particular foam. Two other subjects reported this decrease in itching after a two-time application, and the remaining two subjects reported the decrease in itching after a four-time application.

In ten subjects, the fungal infections were eliminated after a total treatment time of eight days, in six subjects the healing time was eleven days, and in four subjects the healing time was 14 days. It is to be noted that the latter four subjects were the most heavily affected by the fungal infection. No subject could find a difference between the foam created by the SITA measurement method and the foam produced by the "M3 mini foamer".

Examples 6 to 8

In order to investigate the influence of the concentration of active ingredient on the foam formation, the following compositions 6 to 18 were prepared and investigated in regard to the concentrations of active ingredient diclofenac.

| | Ingredient | Composition in wt. % |
|---|---|---|
| 1 | Diclofenac | 1.000 |
| 2 | Propylene glycol | 15.000 |
| 3 | 2-Propanol | 10.250 |
| 4 | Ascorbylpalmitate | 0.020 |
| 5 | Phospholipid foaming agent A | 13.330 |
| 6 | Sodium dihydrogen phosphate dihydrate, ultrapure | 0.120 |
| 7 | Disodium hydrogen phosphate dodecahydrate, cryst. | 0.660 |
| 8 | EDTA | 0.040 |
| 9 | Ultrapure water | 59.380 |
| 10 | Peppermint oil, rectified | 0.200 |
| | TOTAL | 100.00 |

Figure 6:
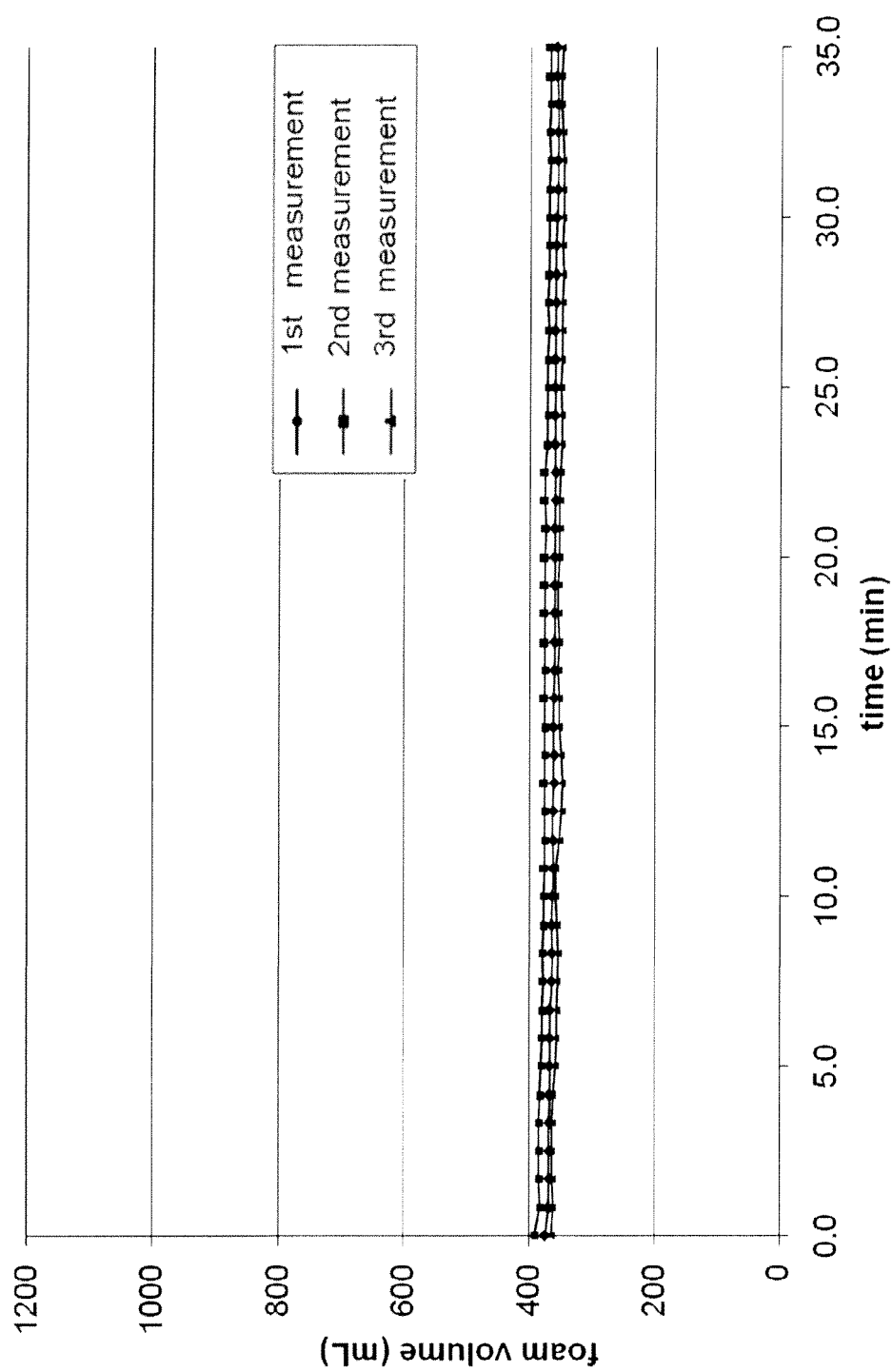

The foam behavior of this composition 6 is shown in FIG. 6.

| | Ingredient | Composition in wt. % |
|---|---|---|
| 1 | Diclofenac | 2.000 |
| 2 | Propylene glycol | 15.000 |
| 3 | 2-Propanol | 10.250 |
| 4 | Ascorbylpalmitate | 0.020 |
| 5 | Phospholipid foaming agent A | 13.330 |
| 6 | Sodium dihydrogen phosphate dihydrate | 0.120 |
| 7 | Disodium hydrogen phosphate dodecahydrate, cryst. | 0.660 |
| 8 | EDTA | 0.040 |
| 9 | Ultrapure water | 58.380 |
| 10 | Peppermint oil, rectified | 0.200 |
| | TOTAL | 100.00 |

Figure 7:
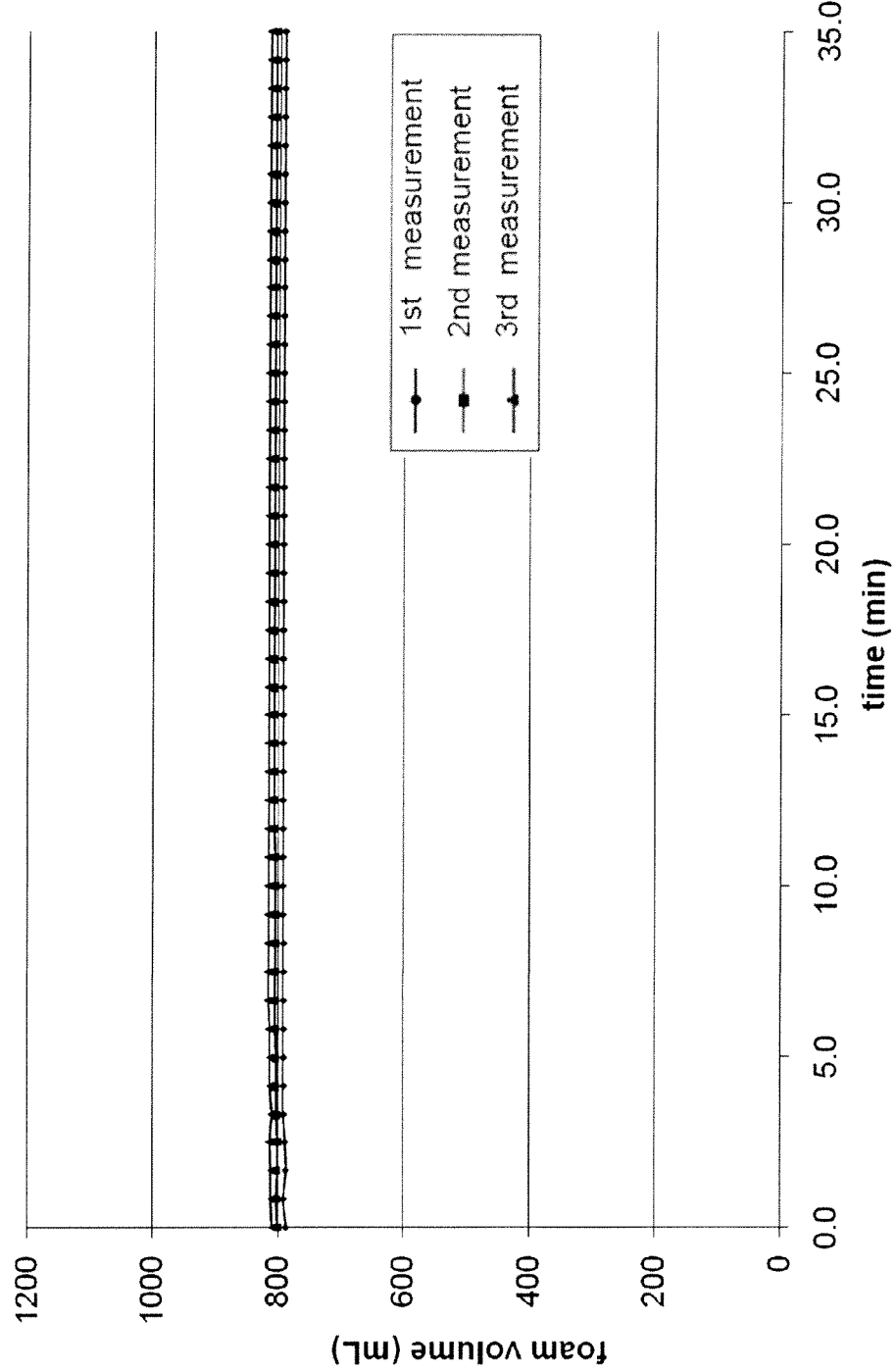

The foam behavior of this composition 7 is shown in FIG. 7.

| | Ingredient | Composition in wt. % |
|---|---|---|
| 1 | Diclofenac | 8.000 |
| 2 | Propylene glycol | 15.000 |
| 3 | 2-Propanol | 10.250 |
| 4 | Ascorbylpalmitate | 0.020 |
| 5 | Phospholipid foaming agent A | 13.330 |
| 6 | Sodium dihydrogen phosphate dihydrate | 0.120 |
| 7 | Disodium hydrogen phosphate dodecahydrate, cryst. | 0.660 |
| 8 | EDTA, Titriplex III | 0.040 |
| 9 | Ultrapure water | 52.380 |
| 10 | Peppermint oil, rectified | 0.200 |
| | TOTAL | 100.00 |

Figure 8:
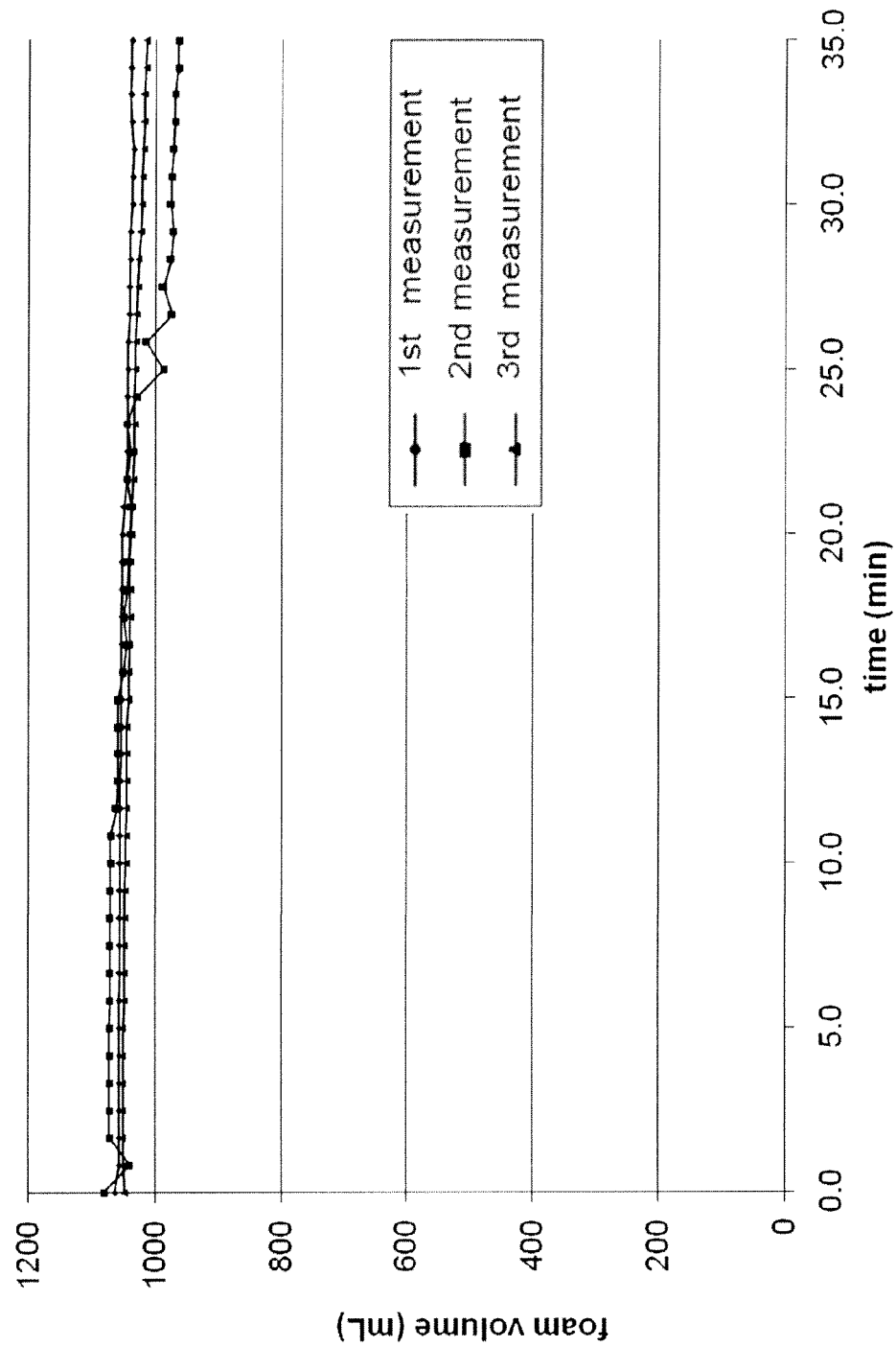

The foam behavior of this composition 8 is shown in FIG. 8.

Based on the comparison of the compositions 6 to 8 and the corresponding FIGS. 6 to 8, one can say that the foam volume increases with practically unchanged foam stability as the concentration of active ingredient increases.

Examples 9 to 11

In order to investigate the influence of the concentration of phospholipid foaming agent on the foam formation, the following compositions 9 to 11 were prepared and investigated in regard to the concentration of phospholipid foaming agent.

| | Ingredient | Composition in wt. % |
|---|---|---|
| 1 | Diclofenac | 4.000 |
| 2 | 1,2-propane diol | 15.000 |
| 3 | 2-Propanol | 10.250 |
| 4 | L (+) ascorbylpalmitate | 0.020 |
| 5 | Phospholipid foaming agent A | 2.000 |
| 6 | Sodium dihydrogen phosphate dihydrate, ultrapure | 0.120 |
| 7 | Disodium hydrogen phosphate dodecahydrate, ultrapure | 0.660 |
| 8 | EDTA | 0.040 |
| 9 | Ultrapure water | 67.710 |
| 10 | Peppermint oil, rectified | 0.200 |
| | TOTAL | 100.00 |

Figure 9:
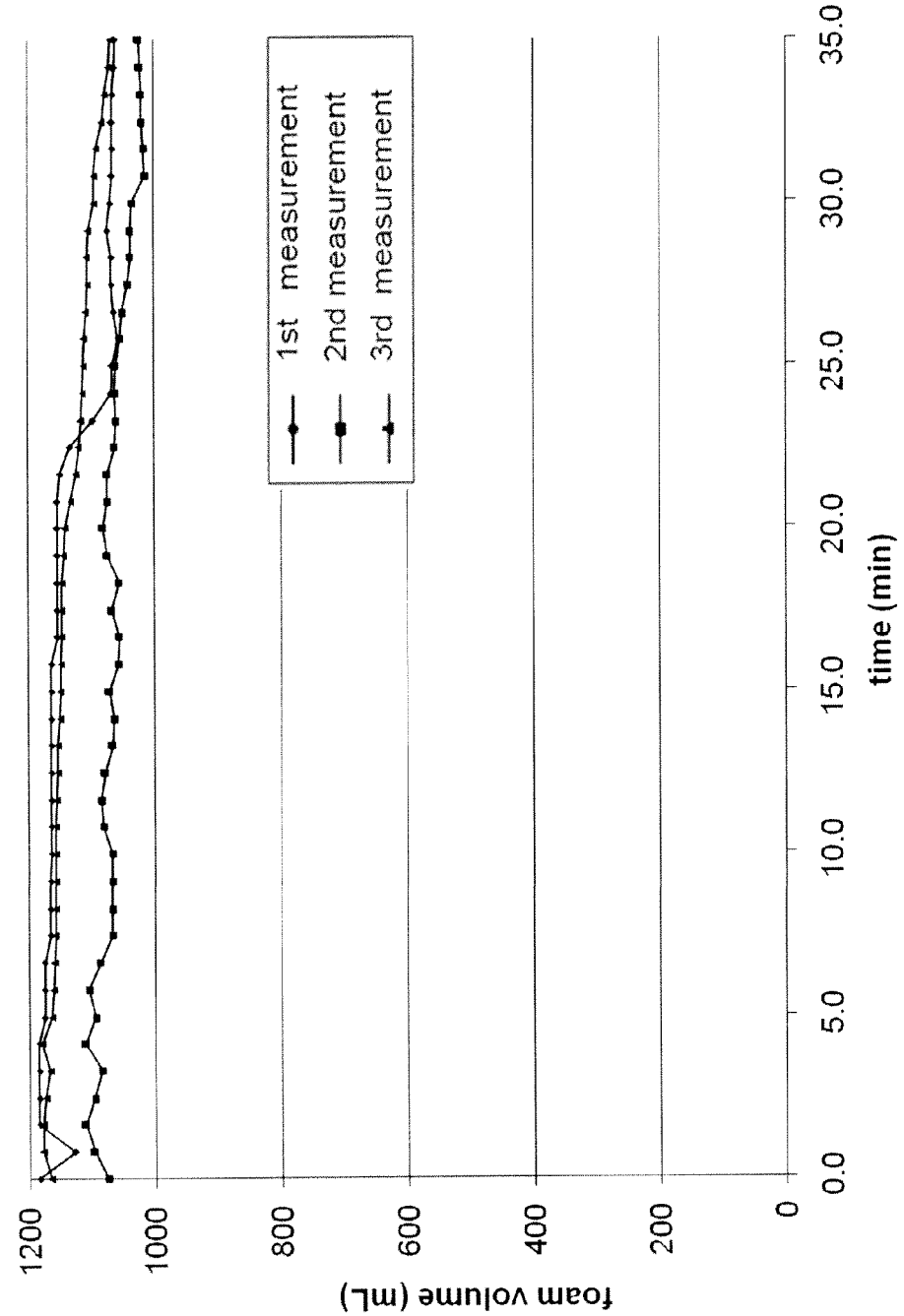

The foam behavior of this composition 9 is shown in FIG. 9.

| | Ingredient | Composition in wt. % |
|---|---|---|
| 1 | Diclofenac | 4.000 |
| 2 | 1,2-propane diol | 15.000 |
| 3 | 2-Propanol | 10.250 |
| 4 | L (+) ascorbylpalmitate | 0.020 |
| 5 | Phospholipid foaming agent A | 5.000 |
| 6 | Sodium dihydrogen phosphate dihydrate, ultrapure | 0.120 |
| 7 | Disodium hydrogen phosphate dodecahydrate, ultrapure | 0.660 |
| 8 | EDTA | 0.040 |
| 9 | Ultrapure water | 64.710 |
| 10 | Peppermint oil, rectified | 0.200 |
| | TOTAL | 100.00 |

Figure 10:
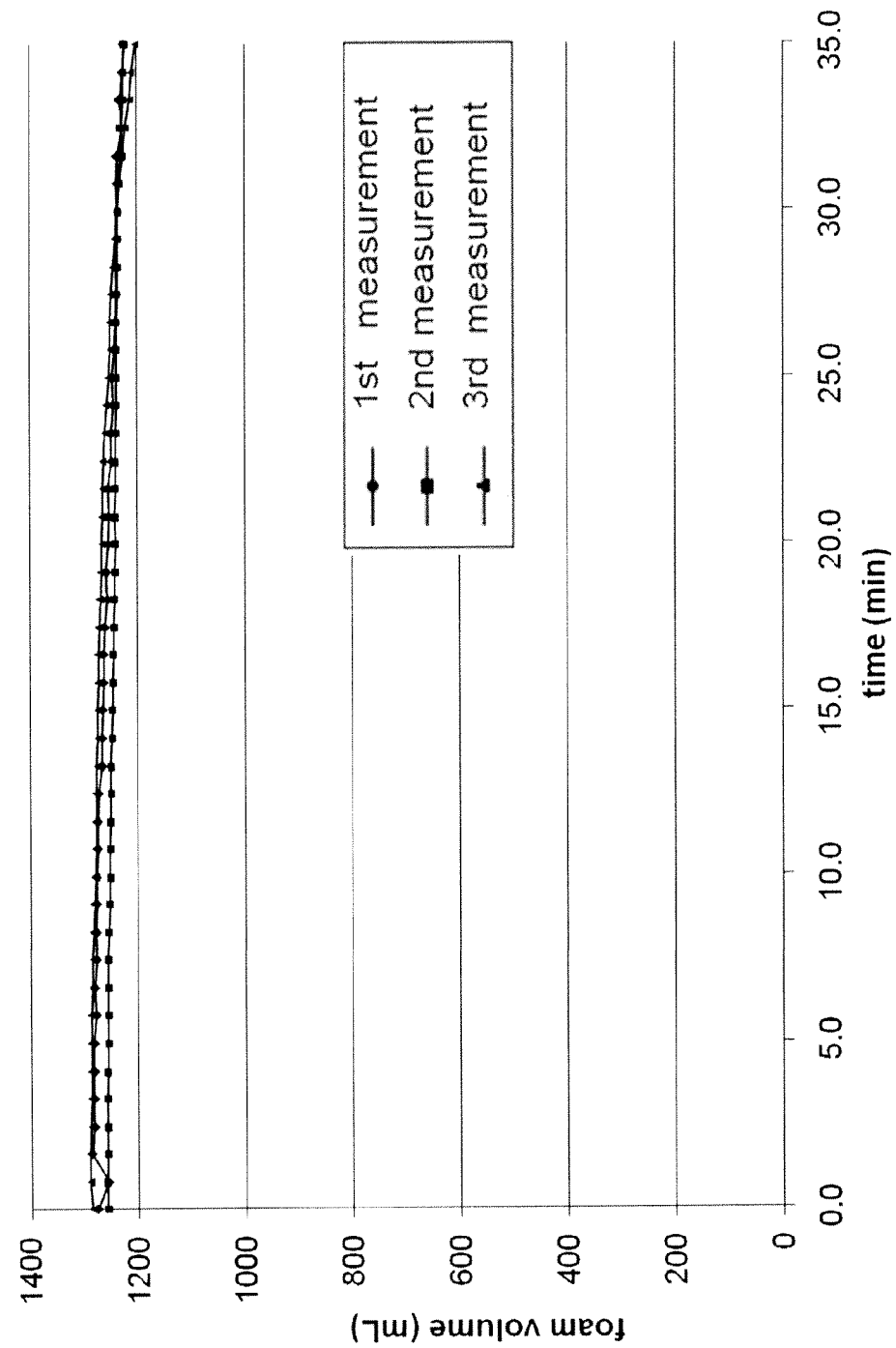

The foam behavior of this composition 10 is shown in FIG. 10.

| | Ingredient | Composition in wt. % |
|---|---|---|
| 1 | Diclofenac | 4.000 |
| 2 | 1,2-propane diol | 15.000 |
| 3 | 2-Propanol | 10.250 |
| 4 | L (+) ascorbylpalmitate | 0.020 |
| 5 | Phospholipid foaming agent A | 20.000 |
| 6 | Sodium dihydrogen phosphate dihydrate, ultrapure | 0.120 |
| 7 | Disodium hydrogen phosphate dodecahydrate, ultrapure | 0.660 |
| 8 | EDTA, Titriplex III | 0.040 |
| 9 | Ultrapure water | 49.710 |
| 10 | Peppermint oil, rectified | 0.200 |
| | TOTAL | 100.00 |

Figure 11:
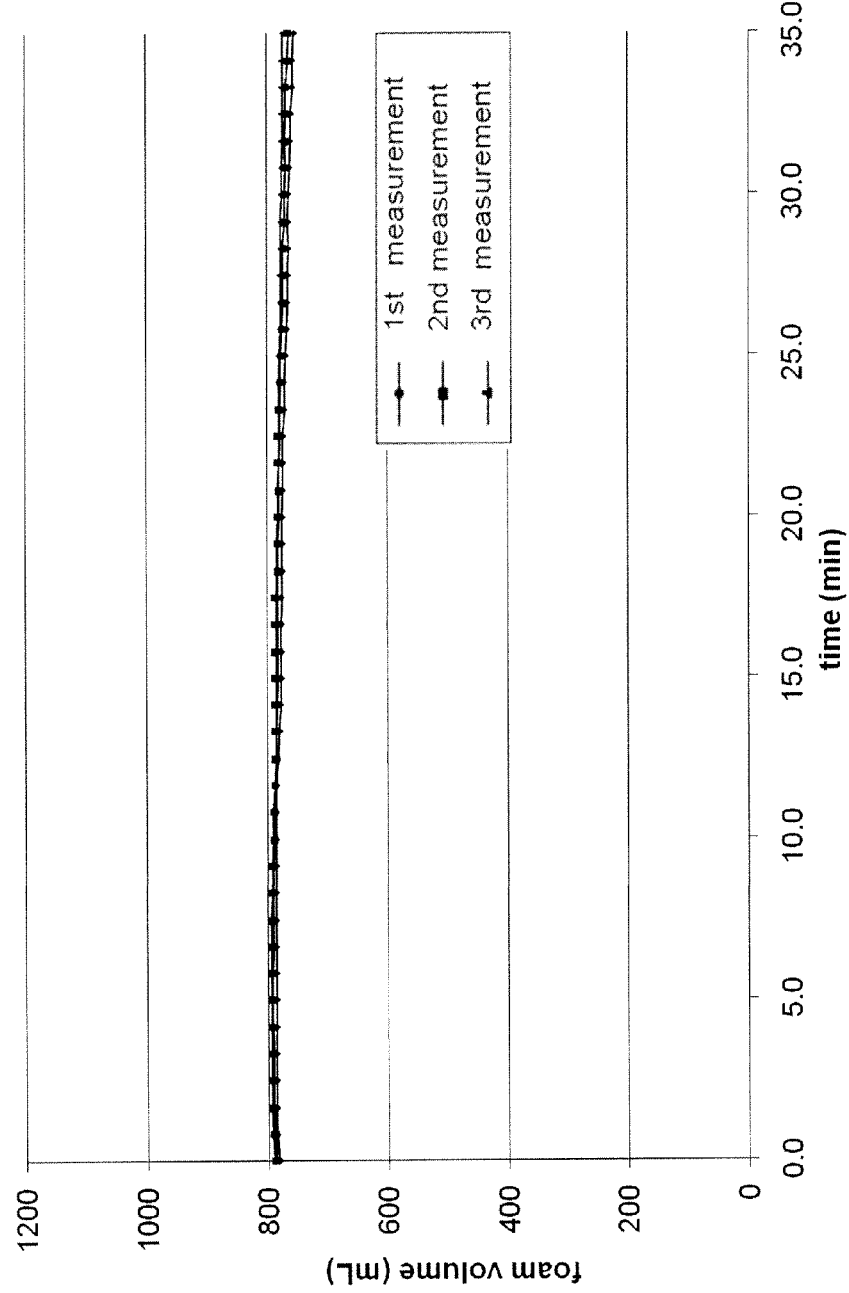

The foam behavior of this composition 11 is shown in FIG. 11.

Based on the comparison of the compositions 9 to 11 and the corresponding FIGS. 9 to 11, one can say that the foam volume decreases with practically unchanged foam stability as the concentration of the phospholipid foaming agent increases.

Examples 12 to 14

In order to investigate the influence of the concentration of isopropanol on the foam formation, the following compositions 12 to 14 were prepared and investigated in regard to the concentration of isopropanol.

| | Ingredient | Composition in wt. % |
|---|---|---|
| 1 | Diclofenac | 4.000 |
| 2 | Propylene glycol | 15.000 |
| 3 | 2-Propanol | 5.000 |
| 4 | Ascorbylpalmitate | 0.020 |
| 5 | Phospholipid foaming agent A | 13.330 |
| 6 | Sodium dihydrogen phosphate dihydrate | 0.120 |
| 7 | Disodium hydrogen phosphate dodecahydrate, cryst. | 0.660 |
| 8 | EDTA | 0.040 |
| 9 | Ultrapure water | 61.630 |
| 10 | Peppermint oil, rectified | 0.200 |
| | TOTAL | 100.00 |

Figure 12:
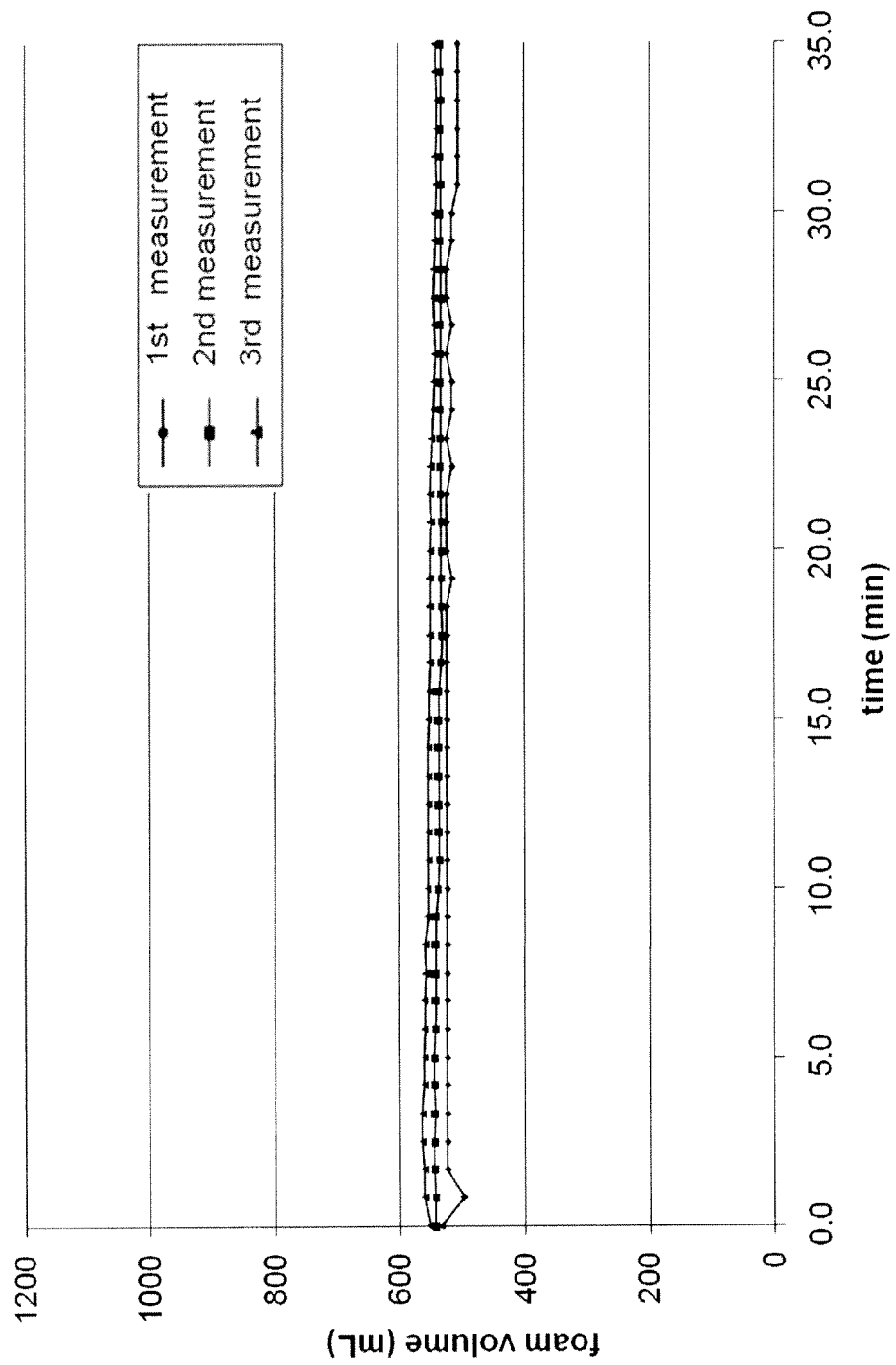

The foam behavior of this composition 12 is shown in FIG. 12.

| | Ingredient | Composition in wt. % |
|---|---|---|
| 1 | Diclofenac | 4.000 |
| 2 | Propylene glycol | 15.000 |
| 3 | 2-Propanol | 10.250 |
| 4 | Ascorbylpalmitate | 0.020 |
| 5 | Phospholipid foaming agent A | 13.330 |
| 6 | Sodium dihydrogen phosphate dihydrate | 0.120 |
| 7 | Disodium hydrogen phosphate dodecahydrate, cryst. | 0.660 |
| 8 | EDTA | 0.040 |
| 9 | Ultrapure water | 56.630 |
| 10 | Peppermint oil, rectified | 0.200 |
| | TOTAL | 100.00 |

Figure 13:
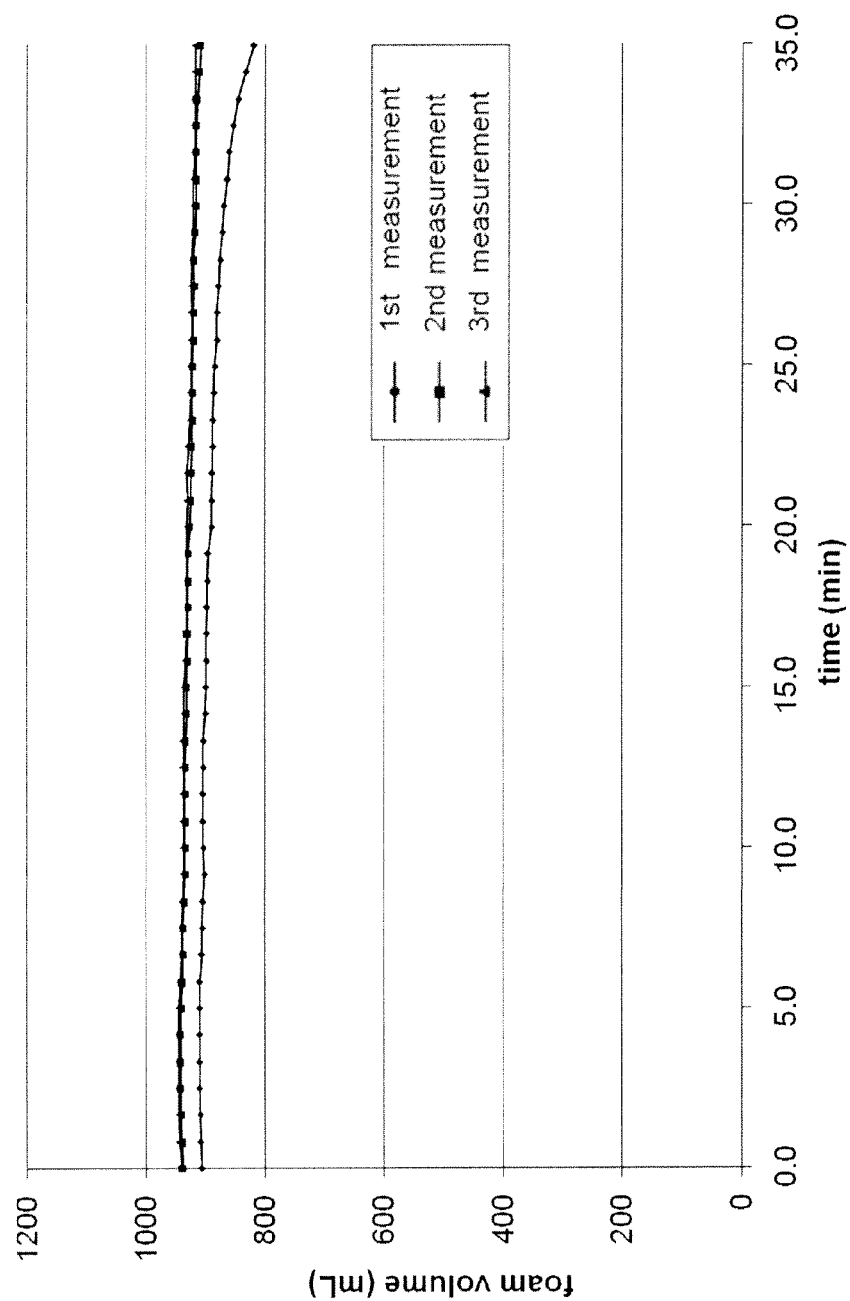

The foam behavior of this composition 13 is shown in FIG. 13.

| | Ingredient | Composition in wt. % |
|---|---|---|
| 1 | Diclofenac | 4.000 |
| 2 | Propylene glycol | 15.000 |
| 3 | 2-Propanol | 20.000 |
| 4 | Ascorbylpalmitate | 0.020 |
| 5 | Phospholipid foaming agent A | 13.330 |
| 6 | Sodium dihydrogen phosphate dihydrate | 0.120 |
| 7 | Disodium hydrogen phosphate dodecahydrate, cryst. | 0.660 |
| 8 | EDTA | 0.040 |
| 9 | Ultrapure water | 46.630 |
| 10 | Peppermint oil, rectified | 0.200 |
| | TOTAL | 100.00 |

Figure 14:
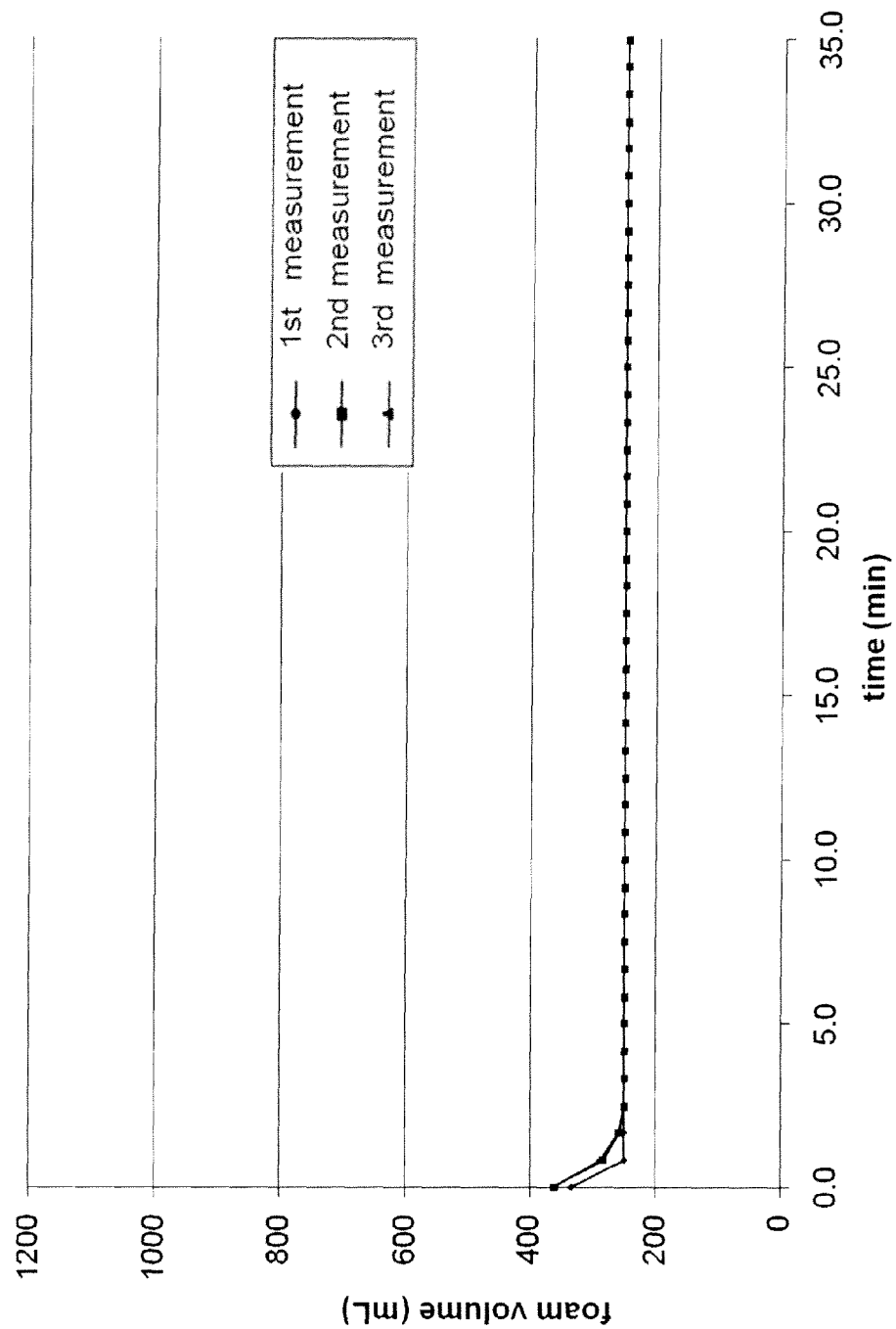

The foam behavior of this composition 14 is shown in FIG. 14.

Based on the comparison of the compositions 12 to 14 and the corresponding FIGS. 12 to 14, one can say that the foam volume increases as a function of the concentration of isopropanol with rising concentration of isopropanol from 5 wt. % to 10 wt. % and then decreases again in the range of 10 wt. % to 20 wt. %, so that no stable foam is formed at a concentration of 20 wt. % of isopropanol. The slight foam volume shown initially in FIG. 14 should be disregarded.

Examples 15 to 17

In order to investigate the influence of the concentration of propylene glycol on the foam formation, the following compositions 15 to 17 were prepared, differing in terms of the concentration of propylene glycol.

| | Ingredient | Composition in wt. % |
|---|---|---|
| 1 | Diclofenac | 4.000 |
| 2 | 1,2-propane diol | 5.000 |
| 3 | 2-Propanol | 10.250 |
| 4 | L (+) ascorbylpalmitate | 0.020 |
| 5 | Phospholipid foaming agent A | 13.330 |
| 6 | Sodium dihydrogen phosphate dihydrate, ultrapure | 0.120 |
| 7 | Disodium hydrogen phosphate dodecahydrate, ultrapure | 0.660 |
| 8 | EDTA | 0.040 |
| 9 | Ultrapure water | 66.380 |
| 10 | Peppermint oil, rectified | 0.200 |
| | TOTAL | 100.00 |

Figure 15:
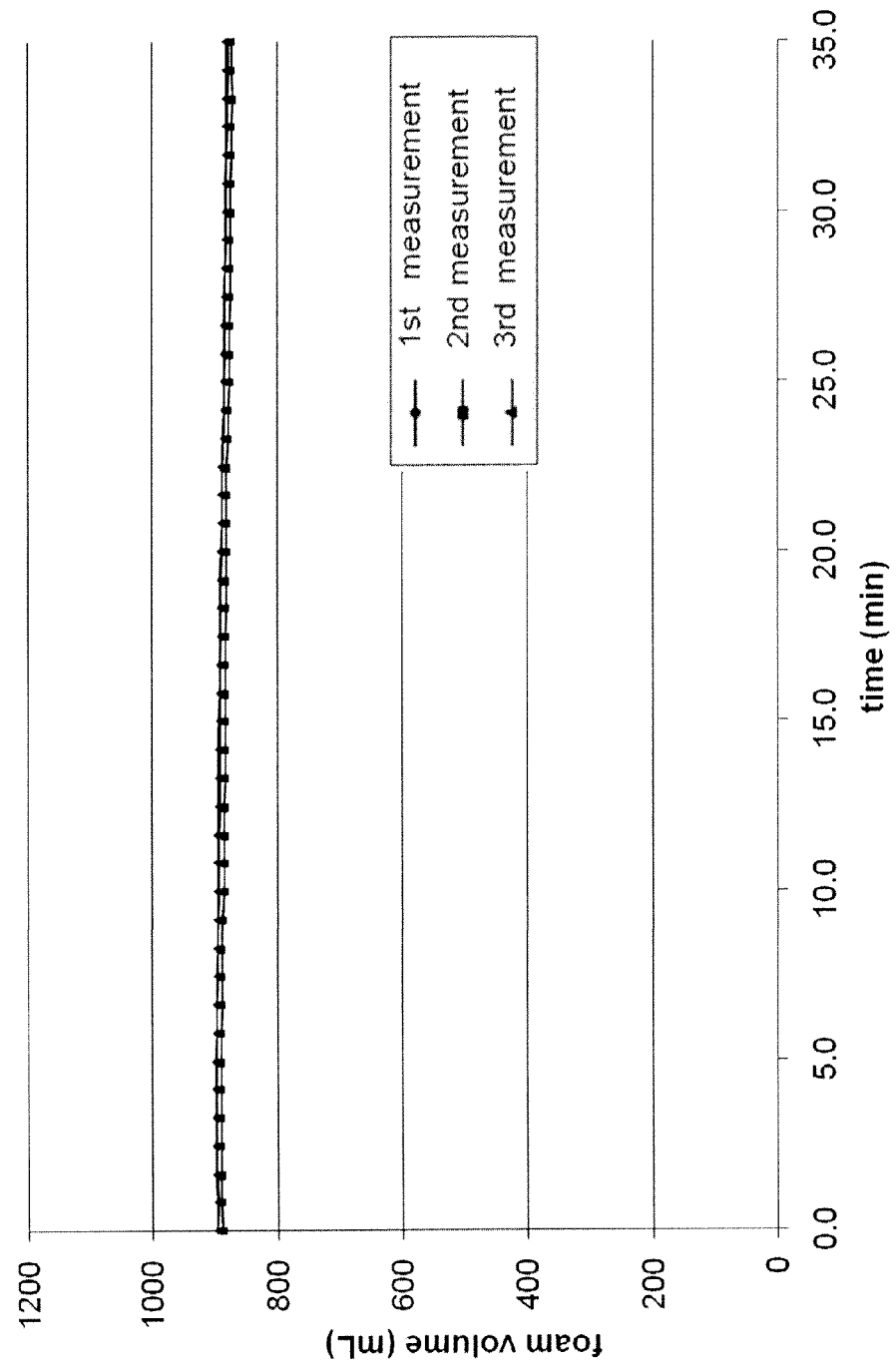

The foam behavior of this composition 15 is shown in FIG. 15.

| | Ingredient | Composition in wt. % |
|---|---|---|
| 1 | Diclofenac | 4.000 |
| 2 | 1,2-propane diol | 10.000 |
| 3 | 2-Propanol | 10.250 |
| 4 | L (+) ascorbylpalmitate | 0.020 |
| 5 | Phospholipid foaming agent A | 13.330 |
| 6 | Sodium dihydrogen phosphate dihydrate, ultrapure | 0.120 |
| 7 | Disodium hydrogen phosphate dodecahydrate, ultrapure | 0.660 |
| 8 | EDTA | 0.040 |
| 9 | Ultrapure water | 61.380 |
| 10 | Peppermint oil, rectified | 0.200 |
| | TOTAL | 100.00 |

Figure 16:
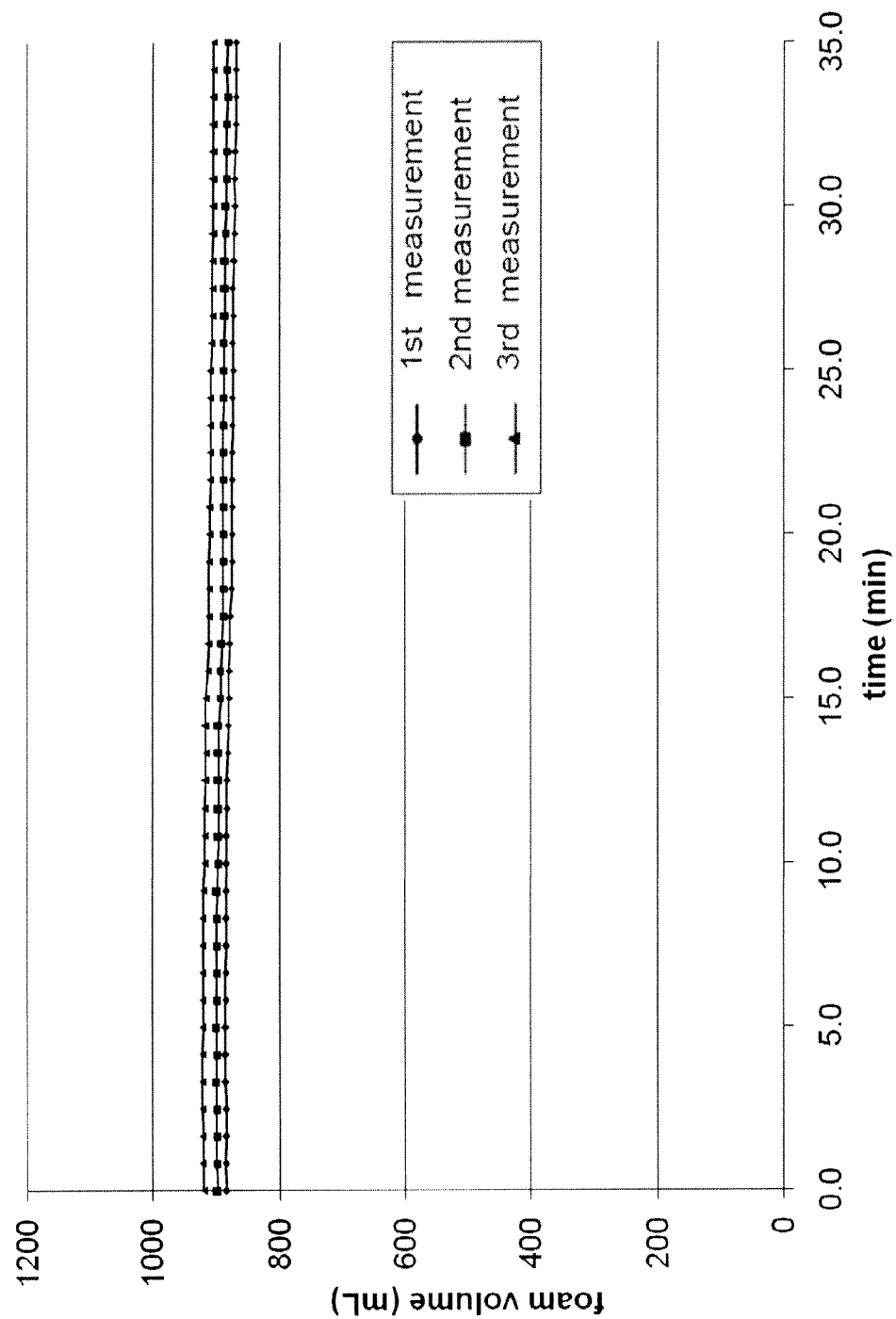

The foam behavior of this composition 16 is shown in FIG. 16.

| | Ingredient | Composition in wt. % |
|---|---|---|
| 1 | Diclofenac | 4.000 |
| 2 | 1,2-propane diol | 20.000 |
| 3 | 2-Propanol | 10.250 |
| 4 | L (+) ascorbylpalmitate | 0.020 |
| 5 | Phospholipid foaming agent A | 13.330 |
| 6 | Sodium dihydrogen phosphate dihydrate, ultrapure | 0.120 |
| 7 | Disodium hydrogen phosphate dodecahydrate, ultrapure | 0.660 |
| 8 | EDTA | 0.040 |
| 9 | Ultrapure water | 51.380 |
| 10 | Peppermint oil, rectified | 0.200 |
| | TOTAL | 100.00 |

Figure 17:
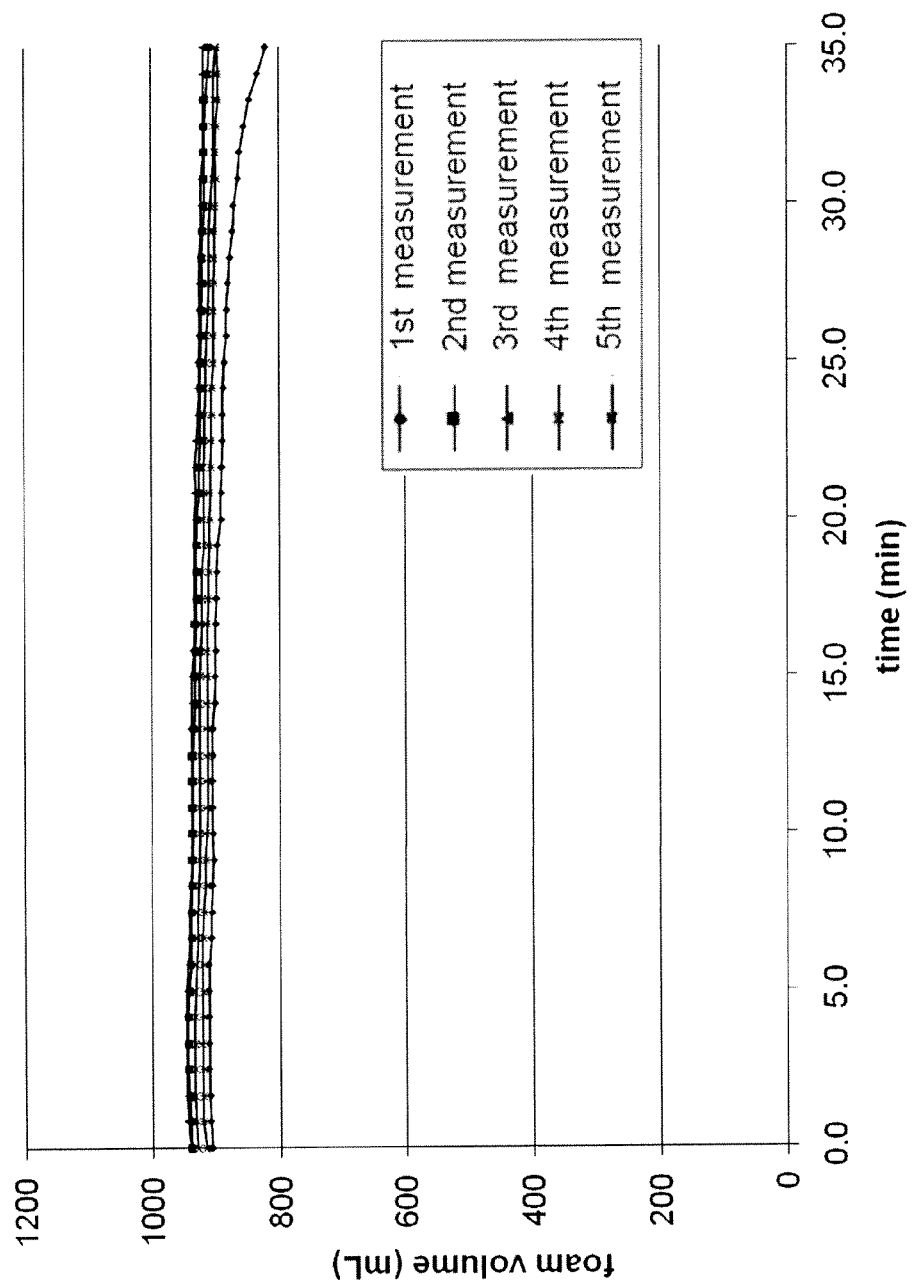
FIG. 17 depicts 5 measurements (as indicated in the legend) foam volume in mL (y-axis) vs. time (minutes) for the composition described in Example 17, below.

The foam behavior of this composition 17 is shown in FIG. 17.

Based on the comparison of the compositions 15 to 17 and the corresponding FIGS. 15 to 17, one can say that the concentration of propylene glycol has little or only a very slight influence on the foam volume and the foam stability.

Example 18

In a comparison investigation on 14 subjects (8 female, 6 male) with pronounced acne in the facial region, the subjects were treated twice daily (morning and evening) with a foam that was made from a composition whose ingredients are quantified in the following table per composition 18.

| | Ingredient | Composition in wt. % |
|---|---|---|
| 1 | Erythromycin | 1.50 |
| 2 | Propylene glycol | 15.00 |
| 3 | 2-Propanol | 9.35 |
| 4 | Phospholipid foaming agent B | 8.00 |
| 5 | Sodium dihydrogen phosphate-dihydrate | 0.50 |
| 6 | Disodium hydrogen phosphate-dodecahydrate cryst. | 1.14 |
| 7 | Sodium hydroxide 10% w/w | 1.00 |
| 8 | Tegosoft GC | 7.70 |
| 9 | Ultrapure water | 55.81 |
| | TOTAL | 100.00 |

Figure 18:
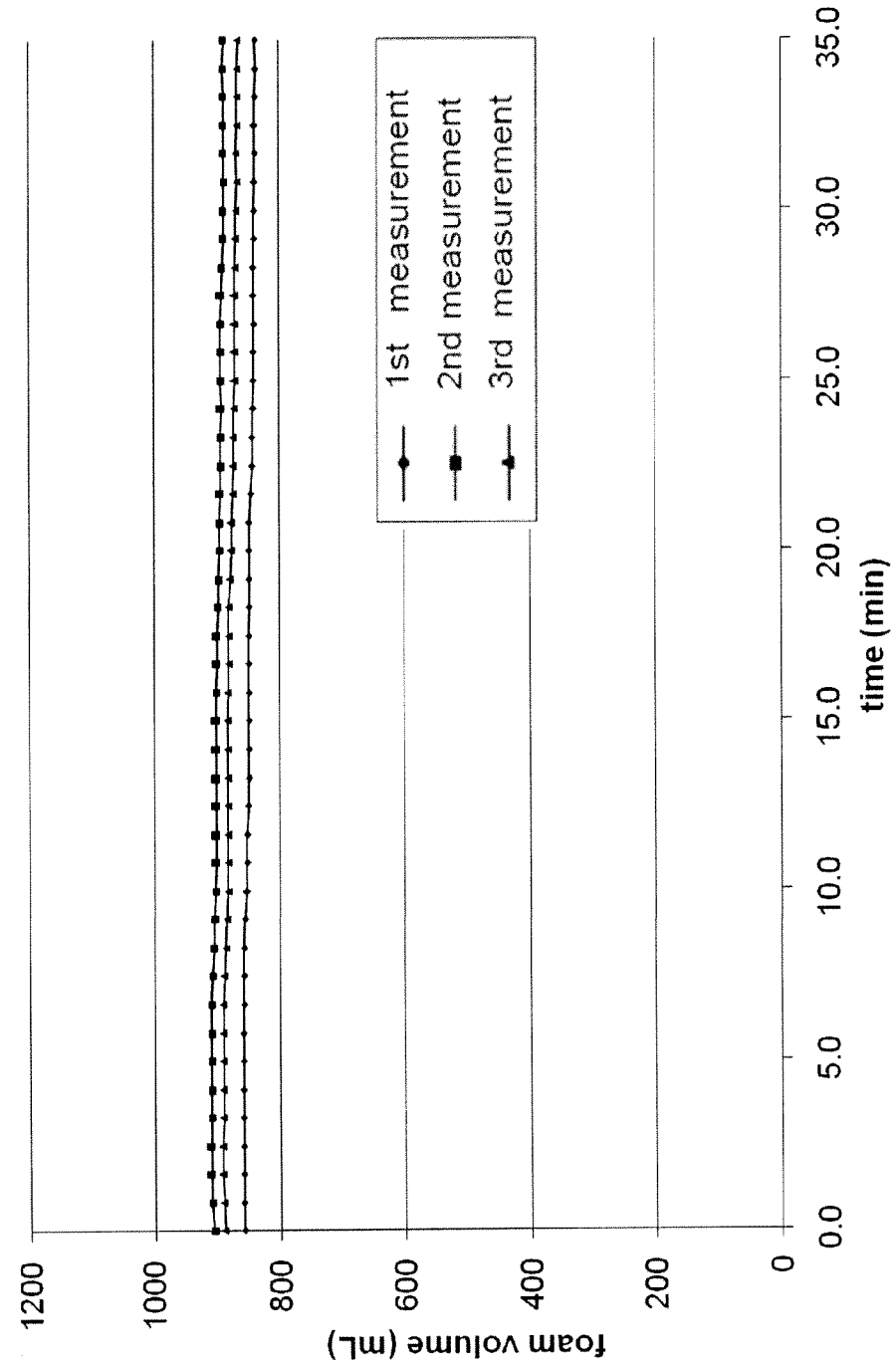
FIGS. 18 and 19 depict 3 measurements (as indicated in the legend) of foam volume in mL (y-axis) vs. time (minutes) for various compositions as described herein.

The foaming behavior of this composition 18 is shown in FIG. 18.

The treatment was done per application with a defined amount of 0.4 mg foam per half of the face. The foam was applied directly to the area being treated and massaged in by circular motions with 2 fingers. The total therapy time amounted to 60 days.

Each time the left half of the face of each subject was treated with the foam made by means of the above-described SITA measurement method and the right half of the face of each subject by means of a foam made with an "M3 minifoamer" of Rexam/Airspray, both foams being prepared from composition 18.

The first success could already be determined for both foams after 30 days application: the lesions on the left side of the face were reduced by around 19% and those of the right half by around 21%.

At the final evaluation on day 60 of the investigation, a decrease in lesions by around 36% was found for the left half of the face and a decrease of around 34% for the right half of the face. It was not possible to determine a significant difference between the two halves of the face. None of the subjects perceived the treatment to be unpleasant or reported painful irritation of the treated areas. Neither could any differences be established in the toleration of the treatment between the two halves of the face.

Sample Embodiment 19

In a double-blind, randomized and placebo-controlled comparative study of 12 subjects (5 female, 7 male) we investigated the efficacy of a) the above-described composition 10, containing 4% diclofenac-sodium, b) of the above-described composition 1, containing 10% ketoprofen, and the efficacy of a ketoprofen-free composition, which was identical to composition 1 in terms of ingredients 2 to 9, this ketoprofen-free composition having no ketoprofen and instead having 10 wt. % more water than composition 1, in the treatment of an artificially induced UV erythema. All foams used were produced by means of the above-described SITA measurement method, as well as the "M3 minifoamer" of Rexam/Airspray, based on the same starting compositions.

The artificial UV erythemas were created at 16 test fields (each one 2×2 cm) on the back, 4 test fields to the left and right of the spinal column, as well as 4 test fields in the upper and lower region of the back. The 8 upper test fields were exposed to a UV dose of 1.5×MED and the lower test fields with 2.5×MED.

After the UV exposure, ECG rings with an inner diameter of 16 mm were glued to the centers of the UV-exposed test fields. The untreated fields were likewise marked with ECG rings. The distance between the test fields was around 3 cm.

Figure 19:
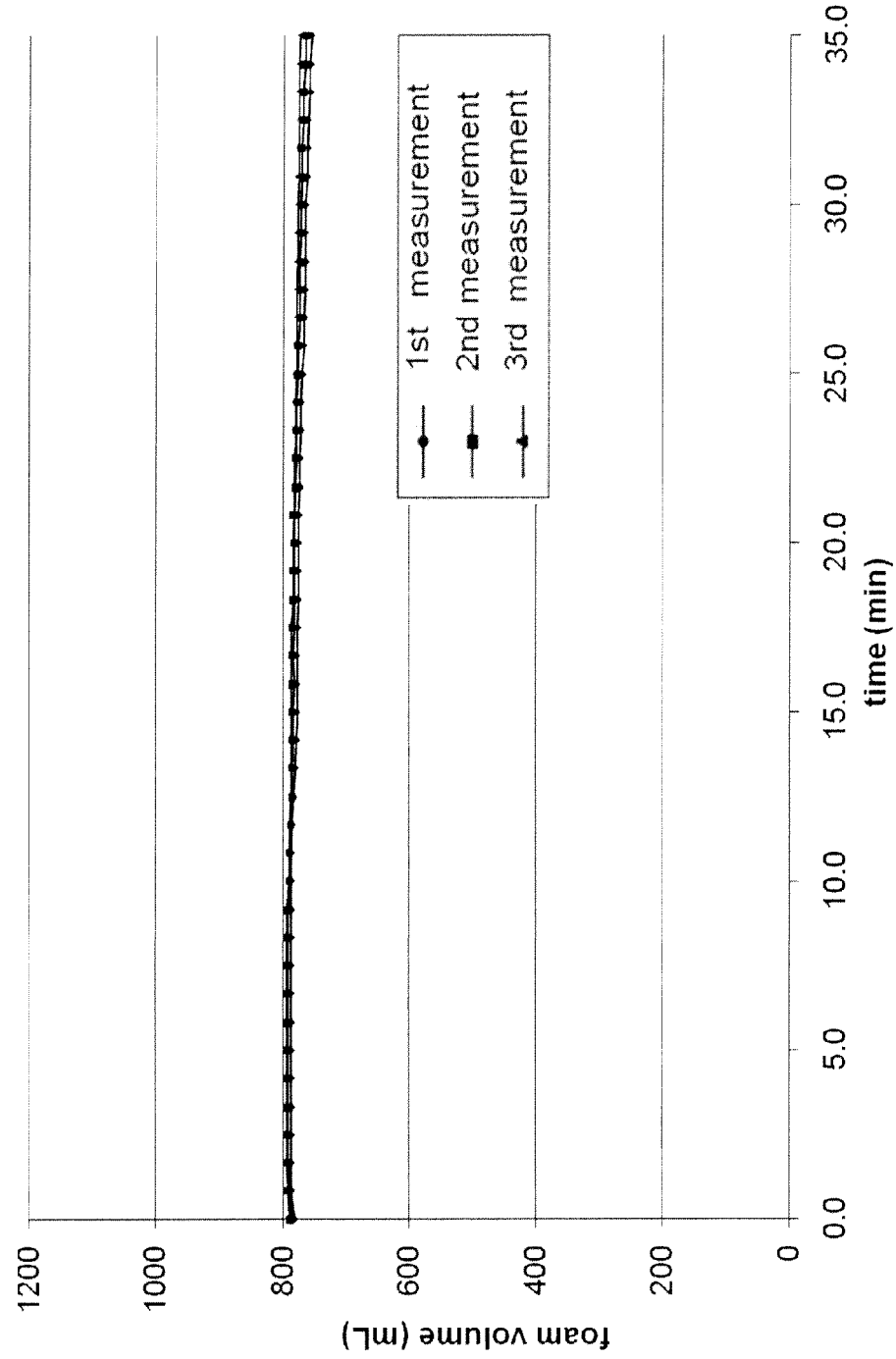

Next, around 10-15 minutes from the end of the UV exposure, a dose of 25 µg foam according to a random list was applied in the ECG rings and evenly distributed using a round spatula. The foam behavior of composition 19 c) (ketoprofen-free composition) is shown in FIG. 19.

Evaluation of the differences was done by the optical examination of a dermatologist. This was based on the internationally recognized visual evaluation method of 0=no visible erythema to 4=intensive erythema for the untreated surface and the evaluation −1=intensive erythema to 3=completely suppressed erythema for the irradiated and treated areas. Checks were done after 2, 3, 4, 5, 6 and 8 hours on the same day as the application.

Between the foams produced according to the SITA measurement method and those using the "M3 minifoamer", a slight difference for the active substance, ketoprofen, was found only at one measurement time point: 6 hours. This difference was not significant. Here, an erythema value of 2 was found for the foam that was made according to the SITA measurement method and a value of 1 for the foam that was made by means of the "M3 minifoamer". No other differences could be found between the foams produced in different ways and containing the active substance.

In comparison with the ketoprofen-free composition (c) and the untreated test fields, the foams containing active substance showed distinct differences at 1.5 MED and 2.5 MED in the final measurement after 8 hours.

Especially at 2.5 MED, a value of 1 was found for the foam containing diclofenac (slight suppression of the erythema, easily identifiable), a value of 2 for the foam containing ketoprofen (distinct suppression of the erythema but still visible) and a value of -1 for the ketoprofen-free foam (more pronounced erythema). The foam made from the composition containing ketoprofen shows a clear therapeutic superiority over the foam containing diclofenac, the ketoprofen-free foam, and the untreated test fields.

All foams containing active substance showed a good toleration. Only for the ketoprofen-free foam were 3 side effects found.

The phospholipid foaming agent A used above in examples 1 and 2, as well as 4 to 17, has the following composition, with the following values referring to the dry substance.

| | |
|---|---|
| Phosphatidyl choline | 80 wt. % ± 10 wt. % |
| Lysophosphatidyl choline | 3 wt. % ± 3 wt. % |
| Phosphatidic acid | ≤8 wt. % |
| Phosphatidyl ethanolamine | ≤4 wt. % |
| Other oily components | max. 6 wt. % |
| Acid number | 2 |
| Peroxide number | 6 |

The phospholipid foaming agent B used above in examples 3 and 18 has the following composition, with the following values referring to the dry substance.

| | |
|---|---|
| Phosphatidyl choline | 85 wt. % ± 10 wt. % |
| Lysophosphatidyl choline | 3 wt. % ± 3 wt. % |
| Tocopherol | max. 0.3 wt. % |
| Acid number | 1 |
| Peroxide number | 5 |

The above indicated peroxide number indicates the milliequivalents of oxygen which are contained in 1000 g of a sample (dry substance). This value, after reacting the sample with potassium iodide in a mixture of chloroform and acetic acid, is determined by titrating the iodine produced in this way with sodium thiosulfate and a potentiometric determination.

The acid number indicates how many mg of potassium hydroxide are needed to neutralize the free, nonesterified fatty acids that are contained in 1 g of phospholipid foaming agent (dry substance). This value is determined by titration of a corresponding dissolved sample with potassium hydroxide solution, using phenolphthalein as indicator.

Equivalents

Those skilled in the art will recognize, or be able to ascertain using no more than routine experimentation, many equivalents to the specific embodiments of the invention described herein. Such equivalents are intended to be encompassed by the following claims.

Incorporation by Reference

The entire contents of all patents, published patent applications, websites, and other references cited herein are hereby expressly incorporated herein in their entireties by reference.

The invention claimed is:

1. A method for making a foamable liquid composition for topical use, comprising:
   a. providing a liquid composition comprising:
      at least one pharmaceutically active agent,
      5 wt. % to 15 wt. % isopropanol,
      at least one further solvent, and
      between 4 wt. % and 15 wt. % of a phospholipid foaming agent comprising 50 wt. % to 95 wt. % phosphatidyl choline, in relation to the dry substance of the phospholipid foaming agent; and wherein the phosphatidyl choline has an acid number of at most 10, a peroxide number of at most 10, and an oil concentration of at most 6 wt. %;
   b. mechanically creating a foam of the liquid composition;
   c. scanning the foam surface to determine the stability and the volume of the foam and thereby determining the foam volume and the foam stability using a SITA measurement method without the use of a propellant;
   d. correlating the foam volume and the foam stability as specified by the SITA measurement method with the pharmaceutical properties of the foam;
   e. varying the concentration of at least one of the pharmaceutically active agent, the isopropanol, the further solvent, or the foaming agent;
   f. repeating steps b through e until 250 ml of the liquid composition, after the mechanical creation of the foam, has a foam density between 0.05 g/ml and 0.8 g/ml, foam volume of at least 400 ml and a foam stability wherein at least about 50% of the foam volume is still present after about 5 minutes at 25° C.

2. The method of claim 1, wherein the at least one further solvent is chosen from the group consisting of water, a monovalent alcohol a polyalcohol, and mixtures thereof.

3. The method of claim 1, the pharmaceutical active ingredient is a further foaming agent.

4. The method of claim 1, wherein the liquid composition further comprises at least one of: a complexing agent, a buffer, a thickening agent, an antioxidant and/or a stabilizer.

5. A foam applicator comprising:
   a liquid composition suitable for topical use comprising:
      between 4 wt. % and 15 wt. % of a phospholipid foaming agent comprising 50 wt. % to 95 wt. % phosphatidyl choline in relation to the dry substance of the phospholipid foaming agent, wherein the phosphatidyl choline has an acid number of at most 10, a peroxide number of at most 10, and an oil concentration of at most 6 wt. %;
      5 wt. % to 15 wt. % isopropanol,
      at least one further solvent; and
      a pharmaceutically acceptable active agent; wherein the foam applicator mechanically foams the liquid composition without an additional propellant; and
      wherein upon mechanical foaming of 250 ml of the liquid composition results in a foam with a foam volume of at least about 400 ml and a foam stability wherein at least about 50% of the foam volume is still present after about 5 minutes at 25° C., as determined using a SITA foam measurement; and wherein the foam has a density of about 0.05 g/ml and about 0.8 g/ml.

6. A foam suitable for topical us, formed by mechanical foaming without use of an additional propellant a liquid composition comprising:
   at least one systemically and/or topically acting pharmaceutical active ingredient,
   5 wt. % to 15 wt. % isopropanol,
   at least one further solvent and
   between 4 wt. % and 15 wt. % of a phospholipid foaming agent comprising 50 wt. % to 95 wt. % phosphatidyl choline in relation to the dry substance of the phospholipid foaming agent, wherein the phosphatidyl choline has an acid number of at most 10, a peroxide number of at most 10, and an oil concentration of at most 6 wt. %,
   wherein the foam so created by foaming 250 ml of the liquid composition has a foam volume of between 450 and 1400 ml,
   wherein the foam stability has, after a dwell time of up to ten minutes between 55% and 100% of the foam volume that was originally present immediately after the creation of the foam, wherein both the foam volume and the foam stability is determined by a standardized SITA foam measurement method, and wherein the foam has a density of about 0.05 g/ml and about 0.8 g/ml.

7. The foam of claim 6, wherein the foam volume is about 600 ml to about 1200 ml.

8. The foam of claim 6, wherein at least about 50% of the foam volume is still present after about 10 minutes.

9. The foam of claim 6, wherein about 55% to about 85% of the foam volume is still present after about 5 minutes after being formed.

10. The foam of claim 6, wherein about 85% to about 100% of the foam is still present after about 10 minutes after being formed.

11. The foam of claim 6, wherein the foam has a density of about 0.15 g/ml and about 0.4 g/ml.

12. The foam of claim 6, wherein the further solvent is selected from the group consisting of water, a monovalent alcohol, a polyalcohol, and mixtures thereof.

13. The foam of claim 6, wherein the active ingredient is selected from the group consisting of local anesthetics, antimycotics, antibiotics, analgesics, nonsteroidal antirrheumatics, nonsteroidal anti-inflammatories, corticoids, immune modulators and salts thereof.

14. The foam of claim 13, wherein the liquid composition comprises between 0.1 wt. % and 20 wt. % of at least one analgesic.

15. The foam of claim 13, wherein the liquid composition comprises between 0.01 wt. % and 10 wt. % of at least one antimycotic.

16. The foam of claim 13, wherein the liquid composition comprises at least one corticoid active ingredient in a concentration between 0.1 wt. % and 5 wt. %.

17. The foam of claim 6, wherein the liquid composition comprises at least one topical anesthetic in a concentration between 3 wt. % and 15 wt. %.

18. The foam of claim 6, wherein the liquid composition comprises an immunomodulator in a concentration between 0.03 wt. % and 0.1 wt. %.

19. The foam of claim 6, wherein the phospholipid foaming agent comprises at most 15 wt. % of lyso-phosphatidyl choline, at most 10 wt. % of phosphatidic acid and at most 10 wt. % of phosphatidyl ethanolamine.

20. The foam of claim 6, wherein the further solvent is propylene glycol, and is present in the composition in a concentration between 2 wt. % and 25 wt. %.

* * * * *